(12) United States Patent
Bush et al.

(10) Patent No.: US 8,163,760 B2
(45) Date of Patent: Apr. 24, 2012

(54) USE OF PYRIDOPYRIMIDINE COMPOUNDS IN THE TREATMENT OF GLIOMAS

(75) Inventors: Ashley Bush, Parkville (AU); Penelope Jane Huggins, Murrumbeena (AU); Jack Gordon Parsons, Brunswick (AU); Gaik Beng Kok, North Carlton (AU); Vijaya Kenche, Oakleigh East (AU)

(73) Assignee: Prana Biotechnology Limited, Parkville, Victoria (AU)

( * ) Notice: Subject to any disclaimer, the term of this patent is extended or adjusted under 35 U.S.C. 154(b) by 184 days.

(21) Appl. No.: 12/306,202

(22) PCT Filed: Jun. 22, 2007

(86) PCT No.: PCT/AU2007/000876
§ 371 (c)(1),
(2), (4) Date: Oct. 15, 2009

(87) PCT Pub. No.: WO2007/147217
PCT Pub. Date: Dec. 27, 2007

(65) Prior Publication Data
US 2010/0069393 A1    Mar. 18, 2010

Related U.S. Application Data

(60) Provisional application No. 60/815,779, filed on Jun. 22, 2006.

(51) Int. Cl.
*A01N 43/54* (2006.01)
*A01N 43/90* (2006.01)
*A01N 43/42* (2006.01)
*A61K 31/517* (2006.01)
*A61K 31/519* (2006.01)
*A61K 31/44* (2006.01)

(52) U.S. Cl. .................. 514/259.4; 514/266.1; 514/300

(58) Field of Classification Search .................. None
See application file for complete search history.

(56) References Cited

U.S. PATENT DOCUMENTS 6,977,255 B2 * 12/2005 Robertson et al. ......... 514/235.2

FOREIGN PATENT DOCUMENTS

| WO | 0056729 A | 9/2000 |
|---|---|---|
| WO | 02060373 A2 | 8/2002 |
| WO | 02100826 A2 | 12/2002 |
| WO | WO 03/072578 A1 | 9/2003 |
| WO | 2004030635 A2 | 4/2004 |
| WO | WO 2004/031161 * | 4/2004 |
| WO | WO 2005/063213 A1 | 7/2005 |
| WO | 2006031806 A2 | 3/2006 |
| WO | WO 2007/064797 A2 | 6/2007 |
| WO | WO 2007/068316 A1 | 6/2007 |
| WO | 2007118276 A1 | 10/2007 |

OTHER PUBLICATIONS

Kennis et la. New 2-substituted 1,2,3,4-tetrahydrobenzofuro[3,2-c]pyridine having highly active and potent central alpha2-antagonistic activity as potentail antidepressants. Bioorganic & Medicinal Chemistry Letters, 10, 2000, 71-74.*
Levin et al. Recent Results Cancer Res., 2007, vol. 174, pp. 205-215 (abstract attached).*
Vippagunta et al. Advanced Drug Reviews, 48, 2001.*
Stella et al. (Prodrugs: Challenges and Rewards, Part 1, 2007).*
Han (Advances in Characterization of Pharmaceutical Hydrates. Trends in Bio/Pharmaceutical Industry, pp. 25-29, Mar. 2006).*
Chen, D. et al., "Clioquinol, a Therapeutic Agent for Alzheimer's Disease, Has Proteasome-Inhibitory, Androgen Receptor-Suppressing, Apoptosis-Inducing, and Antitumor Activities in Human Prostate Cancer Cells and Xenografts" Cancer Research (2007) pp. 1636-1644, vol. 67(4).
Bandyopadhyay, S. et al., "Metal Specificity of an Iron-Responsive Element in Alzheimer's APP mRNA 5'Untranslated Region, Tolerance of SH-SY5Y and H4 Neural Cells to Desferrioxamine, Clioquinol, VK-28, and a Piperazine Chelator" Journal of Neural Transmission (2006) pp. 237-247, vol. 71.
Ding, W-Q. et al., "Anticancer Activity of the Antibiotic Clioquinol" Cancer Research (2005) pp. 3389-3395, vol. 65(8).
Fan, L. et al., "Inhibition of N-myc Expression and Induction of Apoptosis by Iron Chelation in Human Neuroblastoma Cells" Cancer Research (2001) pp. 1073-1079, vol. 61.
Chalmers, A. et al., "Investigating the role of Poly(ADP-Ribose) Polymerase-1 in the Response of Glioma Cells to Low Doses of Ionising Radiation" British Journal of Cancer (2002) pp. S31, vol. 86 (Suppl I).

* cited by examiner

*Primary Examiner* — Brandon Fetterolf
*Assistant Examiner* — Anna Pagonakis
(74) *Attorney, Agent, or Firm* — Scully, Scott, Murphy & Presser, P.C.

(57) ABSTRACT

The present invention relates generally to therapeutic agents, formulations comprising them and their use in the treatment, amelioration and/or prophylaxis of glioma brain tumors and related conditions. The therapeutic agent comprises two fused 6-membered rings with at least a nitrogen at position 1 and a hydroxyl at position 8.

9 Claims, 9 Drawing Sheets

Compound A  Compound N

Compound I

Compound O

Compound U  Compound X

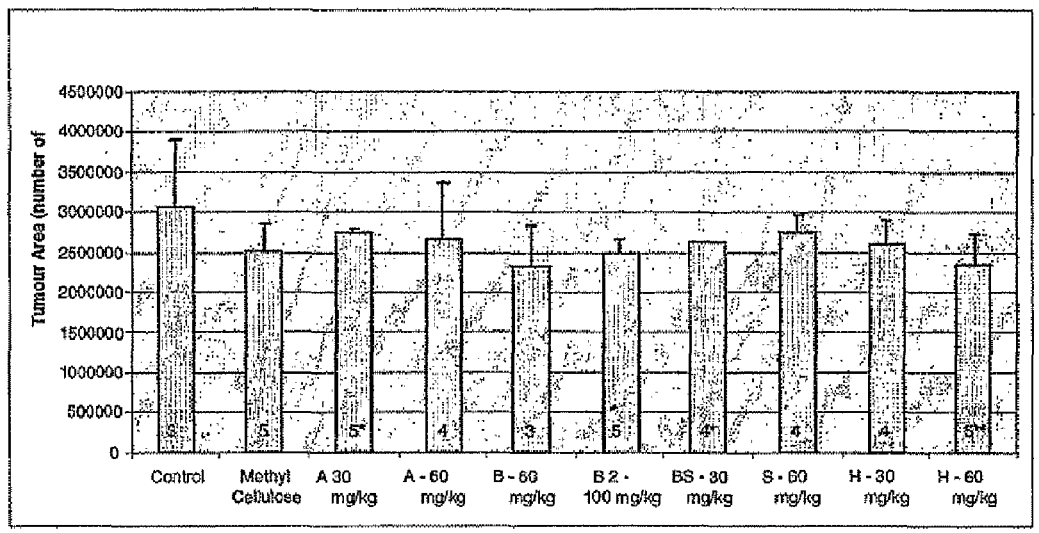
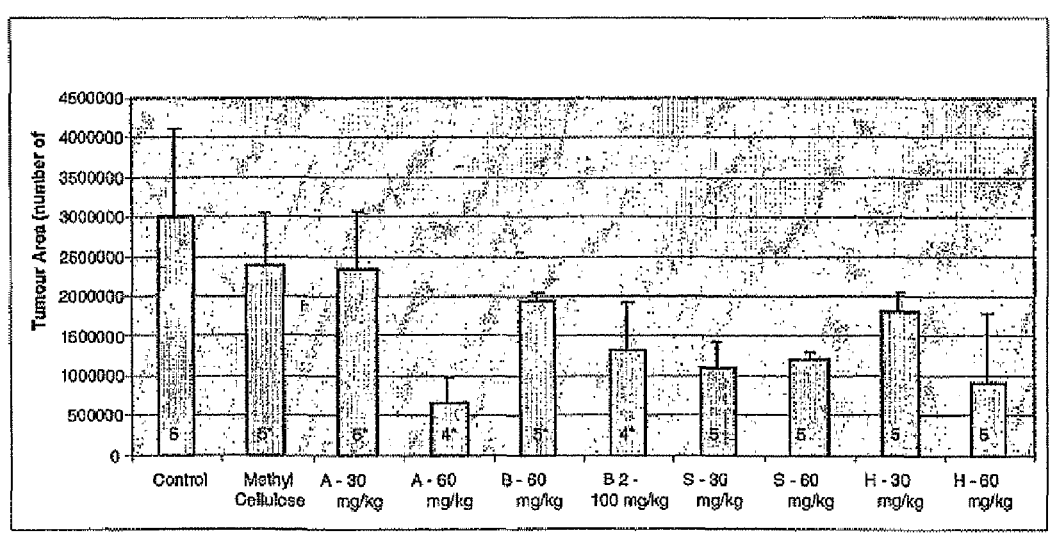
Fig. 6a-b c
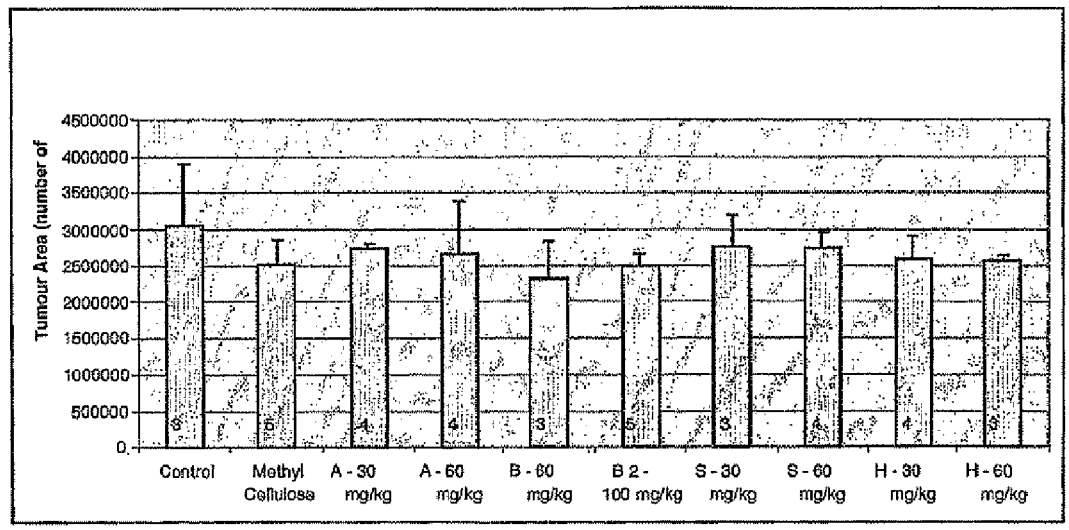
d
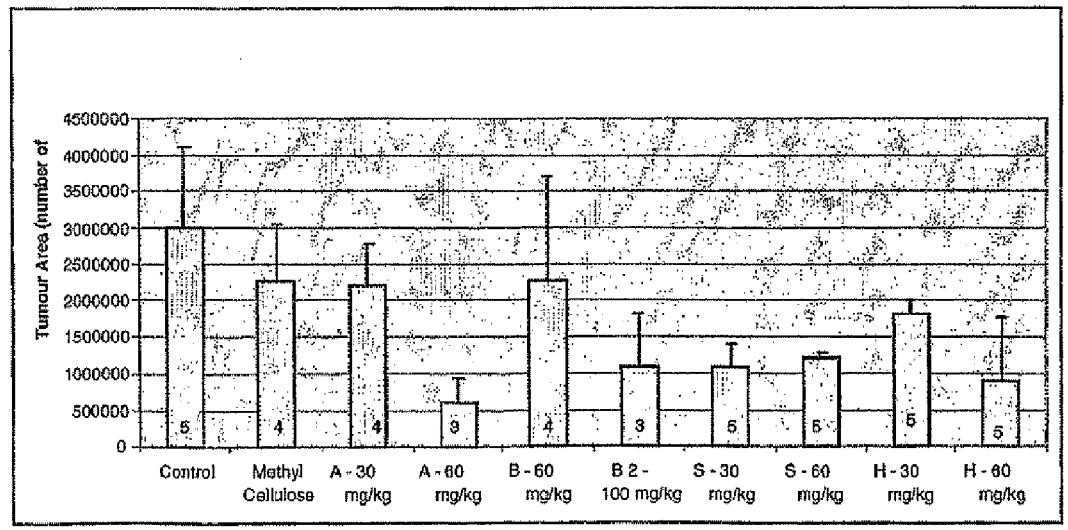
Fig. 6c-d

USE OF PYRIDOPYRIMIDINE COMPOUNDS IN THE TREATMENT OF GLIOMAS

CROSS-REFERENCE TO RELATED APPLICATIONS

This application claims the benefit of U.S. Provisional application No. 60/815,779 filed on Jun. 22, 2006.

BACKGROUND

1. Field

The present invention relates generally to therapeutic agents, formulations comprising them and their use in the treatment, amelioration and/or prophylaxis glioma brain tumours and related conditions.

2. Description of the Prior Art

Cancer is a significant human health problem throughout the world and is one of the largest single causes of mortality and morbidity. The term "cancer" describes an array of different diseases linked by cumulative multiple genetic mutations, which result in the activation of oncogenes and/or the inactivation of tumor suppressor genes. The cause and source of these mutations differs between different cancers of human body organs.

Cancer within the human brain constitutes a very specific, serious and commonly terminal disease, with a median survival in patients of less than 1 year, despite provision of the optimal treatment available. The very unique biological environment of the brain, as separated by the blood brain barrier (BBB), significantly contributes to a range of site-specific cancers in this organ that require alternative treatment than those cancers of the remaining human body.

Approximately 17,000 primary brain tumors are diagnosed in patients in the United States alone each year. Of these, approximately 60% are glioma tumors or 'astrocytomas' that arise from brain cells called astrocytes or their precursors. Astrocytes are cells in the central nervous system that support neuronal function. Astrocytomas can be graded by histologic features that signify increasing malignancy into astrocytoma, anaplastic astrocytoma, or glioblastoma multiforme (GBM). Anaplastic astrocytoma and GBM are considered high-grade gliomas while the astrocytoma is considered to be a low-grade glioma. High-grade tumors grow rapidly and can easily infiltrate and spread through the brain. High-grade tumors are much more aggressive and require very intense therapy. The majority of astrocytic tumors in children are low-grade, whereas the majority in adults are high-grade. Astrocytomas can occur anywhere in the brain and spinal cord, however the majority are located in the cerebral hemispheres.

Patients with brain cancer most commonly present with seizures and a slowly progressive neurologic deficit, usually motor weakness. Alternatively, patients may present with generalized symptoms of increased intracranial pressure, including headaches, nausea and vomiting, and cognitive impairment.

Although advances have been made in detection and therapy of brain cancer diseases, no universally successful method for prevention or treatment is currently available. Current therapies for many brain cancers are generally based on a combination of chemotherapy or surgery and radiation and continue to prove inadequate in many patients.

For example, the treatment of glioma brain tumours remains difficult in that no contemporary treatments are curative. Treatments are non-curative primarily due to tumors being beyond the reach of local control when it is first detected clinically or radiographically. No significant advancements in the treatment of brain cancers have occurred in the past 25 years. Without therapy, patients with GBMs uniformly die within 3 months. Patients conversely treated with optimal therapy, including surgical resection, radiation therapy, and chemotherapy, have a median survival of approximately 1 year. Therefore, the treatment of patients with brain cancer is often palliative and encompasses and/or surgery, radiotherapy, and chemotherapy.

Radiation therapy in addition to surgery has been shown to prolong survival in patients with brain cancers compared to surgery alone, however the responsiveness of these cancers to radiotherapy varies. In many instances, radiotherapy can induce a phase of remission, often marked with stability or regression of neurologic deficits as well as diminution in the size of the contrast-enhancing mass. Unfortunately, any period of response is often short-lived in brain cancer because the tumor typically recurs within 1 year, resulting in further clinical deterioration.

Chemotherapeutic regimens for brain cancer have suggested that fewer than 25% of patients obtain a significant survival benefit from adjuvant chemotherapy. Carmustine (BCNU) and cis-platinum (cisplatin) have been the primary chemotherapeutic compounds used against malignant gliomas. All agents in use have no greater than a 30-40% response rate, and most fall into the range of 10-20%. A major hindrance to the use of chemotherapeutic compounds for brain tumours is the fact that the BBB effectively excludes many agents from the CNS. Despite initial attempts investigating the delivery of chemotherapeutic compounds via an intraarterial route rather than intravenously, no survival advantage has been observed.

The extent of surgery (biopsy versus resection) has been shown in a number of studies to affect length of survival. For example, patients with high-grade gliomas who had a gross total resection had a 2-year survival rate of 19%, while those with a subtotal resection had a 2-year survival rate of 0%.

As many brain cancers cannot be cured with surgery, the surgical goals are to establish a pathological diagnosis, relieve mass effect, and, if possible, achieve a gross total resection to facilitate adjuvant therapy.

Stereotactic biopsy followed by radiation therapy has been considered in certain circumstances. These include patients with a tumor located in an eloquent area of the brain; patients whose tumors have minimal mass effect or are infiltrating without discrete margins; and patients in poor medical condition, precluding general anesthesia. Median survival after stereotactic biopsy and radiation therapy is reported to be from 27-47 weeks.

In light of the foregoing, new approaches for the management of glioblastomas and other glioma brain tumours are critically necessary.

SUMMARY

The present invention is predicated in part on the determination that particular agents are effective in inhibiting the development of glioma brain tumours and related conditions in humans. Hence, the present invention contemplates the use of an agent which comprises a compound having two fused 6-membered rings with at least a nitrogen at position 1 and a hydroxy at position 8 to reduce the growth of glioma brain tumours and in particular glioblastomas (GBM) in human subjects. The present invention is particularly useful for treating or preventing or otherwise reducing the risk of development of GBM, however, the present invention extends to the treatment of any glioma brain tumour including astrocytomas, anaplastic astrocytoma, mixed glioma, oligodendroglioma and other gliomas.

The agent of the present invention may possess one or more of the following properties: crosses the BBB, exhibits reduced adverse side affects; stable in aqueous environments; selectively cytotoxic to cancer cells; and exhibits reduced cytotoxicity to non-malignant cells. Preferably, the agent has two or more, three or more or four or more or five or more of the above-listed properties. In addition, the agent may be selected on the basis that it acts synergistically with another agent such as a chemotherapeutic, immunological or cytokine agent.

Useful agents comprise compounds of the formula (I) which are described in detail below.

In a first aspect there is provided a method for the treatment, amelioration and/or prophylaxis of a glioma brain tumour which comprises administration of an effective amount of an agent which comprises a compound of formula (I):

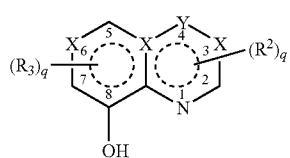

(I)

in which $R^2$ is H; optionally substituted $C_{1-6}$ alkyl; optionally substituted $C_{2-6}$ alkenyl; optionally substituted $C_{2-6}$ alkynyl; optionally substituted $C_{3-6}$ cycloalkyl; optionally substituted aryl; optionally substituted heterocyclyl; CN; $OR^6$, $SR^6$, $COR^6$, $CSR^6$, $HCNOR^6$ or $HCNNR^6$ in which $R^6$ is H, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl or optionally substituted heterocyclyl; $NR^8R^9$ or $SO_2NR^8R^9$ in which $R^8$ and $R^9$ are independently selected from H, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl and optionally substituted heterocyclyl; $CONR^9R^{10}$ in which $R^9$ is as defined above and $R^{10}$ is optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl or optionally substituted heterocyclyl; $CH_2CONR^8R^9$ in which $R^8$ and $R^9$ are as defined above; and $(CH_2)NR^9R^{11}$ in which $R^9$ is as defined above and $R^{11}$ is selected from optionally substituted $C_{1-6}$ alkyl, optionally substituted $C_{2-6}$ alkenyl, optionally substituted alkynyl, optionally substituted $C_{3-6}$ cycloalkyl, optionally substituted aryl, optionally substituted heterocyclyl and $SO_2R^{12}$ in which $R^{12}$ is optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl or optionally substituted heterocycyl and n is 1 to 6;

$R^3$ is selected from H, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl, optionally substituted heterocycyl, optionally substituted $C_{1-6}$ alkoxy, optionally substituted acyl, hydroxy, optionally substituted amino, optionally substituted thio, optionally substituted sulphonyl, optionally substituted sulphinyl, optionally substituted sulphonylamino, halo, $SO_3H$, amine, CN, $CF_3$ and halo.

X is CH or N;
Y is CH, CO, CS or N; and
q is 1, 2 or 3,
salts, hydrates, solvates, derivatives, pro-drugs, tautomers and/or isomers thereof to a subject in need thereof.

The present invention particularly extends to glioma forms of brain tumours such as astrocytoma, GBM, anaplastic astrocytoma, mixed glioma and oligodendroglioma.

Of the gliomas, GBM is particularly treatable with the agents disclosed herein. A defined or specific dosage amount may be administered.

There is also provided a specific dosage range to inhibit growth or viability of cells associated with a glioma in the brain. The dosage range includes from about 1 ng to about 1 g per subject per administration. The administration may be a single dose or a series of divided doses.

There is further provided use of an agent which comprises the compound of formula (I) defined above in the manufacture of a medicament for the treatment, amelioration and/or prophylaxis of a glioma brain tumour.

There is still further provided use of an agent which comprises the compound of formula (I) defined above for the treatment, amelioration and/or prophylaxis of a glioma brain tumour.

Combination therapy also forms part of the present invention in which two or more agents are administered or an agent and another active such as a chemotherapeutic compound, a cytokine, genetic molecule, an anti-oxidant and/or an anaesthetic.

Reference to a "chemotherapeutic compound" includes a chemical compound, immunological compound, natural product or sRNAi complex or a product of an introduced viral vector.

Although, the preferred subject is a human, the present invention has application in the veterinary and animal husbandry industries and hence extends to non-human animals.

In a second aspect, there is provided a formulation comprising an agent which comprises the compound of formula (I) defined above for treating, ameliorating and/or preventing a glioma brain tumour.

BRIEF DESCRIPTION OF FIGURES

FIGS. 6a to d are graphs showing effects of compounds A, B, S and H in the C6 glioma model (a,c) and the SMA560 glioma model (b,d).

DETAILED DESCRIPTION

Compounds

Figure 1:
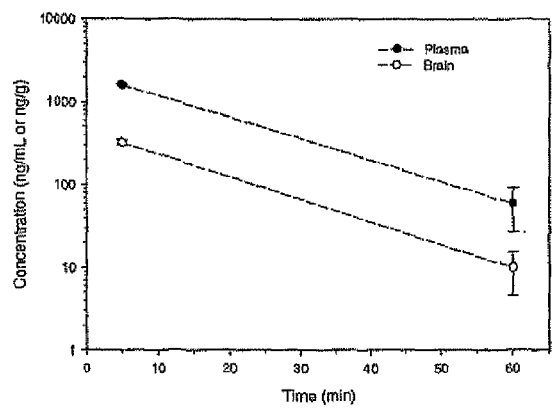
FIG. 1 is a graph showing the brain and plasma concentrations of compounds following IV administration to Swiss Outbred mice at a nominal does of 5 mg/kg. Data is presented as mean 1SD (n=3). The compounds are designated by letter and are defined in the specification.
Figure 1:
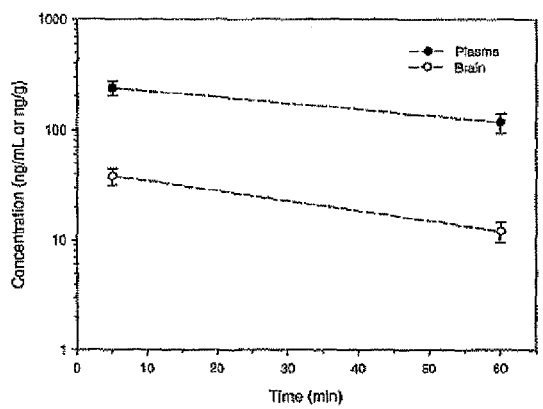
Figure 1:
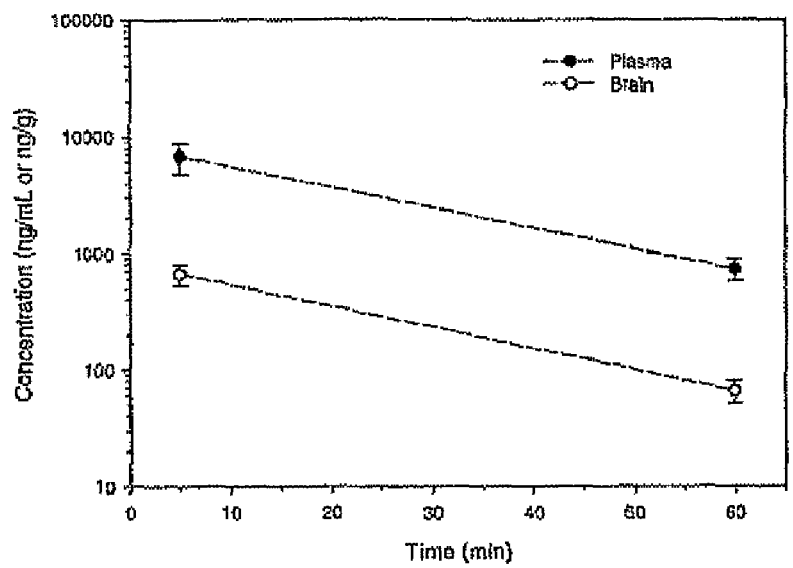
Figure 1:
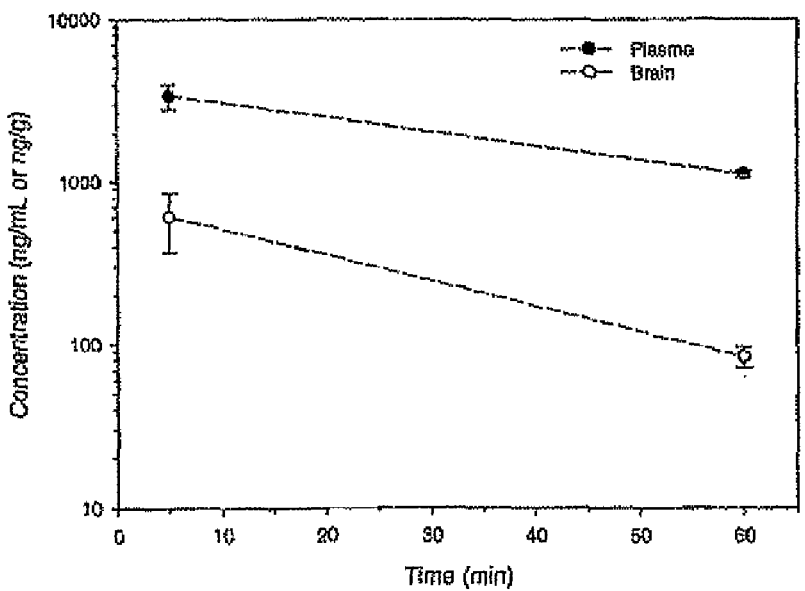
Figure 1:
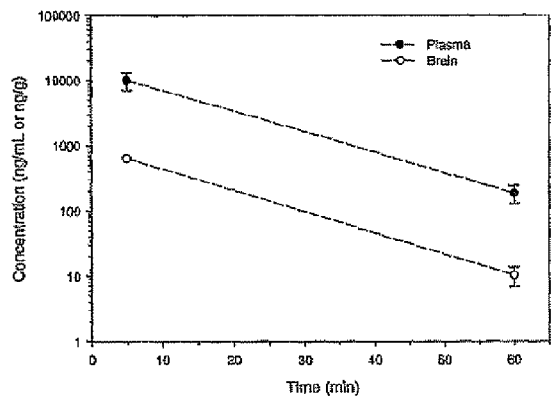
Figure 1:
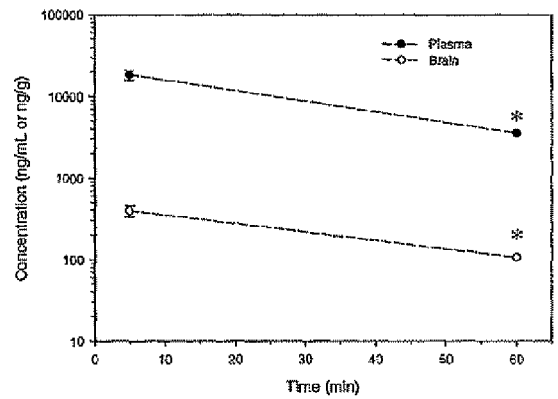
Figure 1:
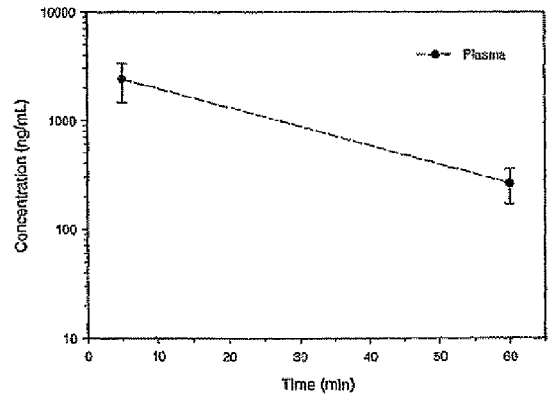
Figure 1:
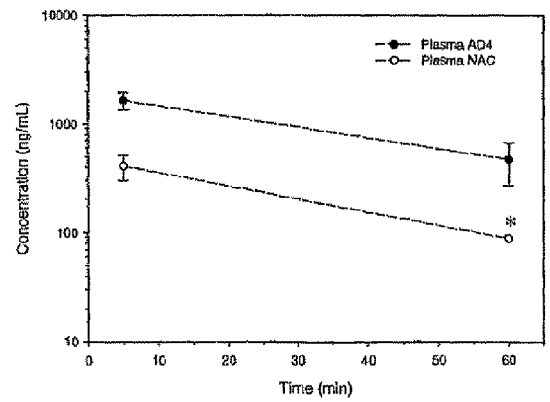
Figure 2:
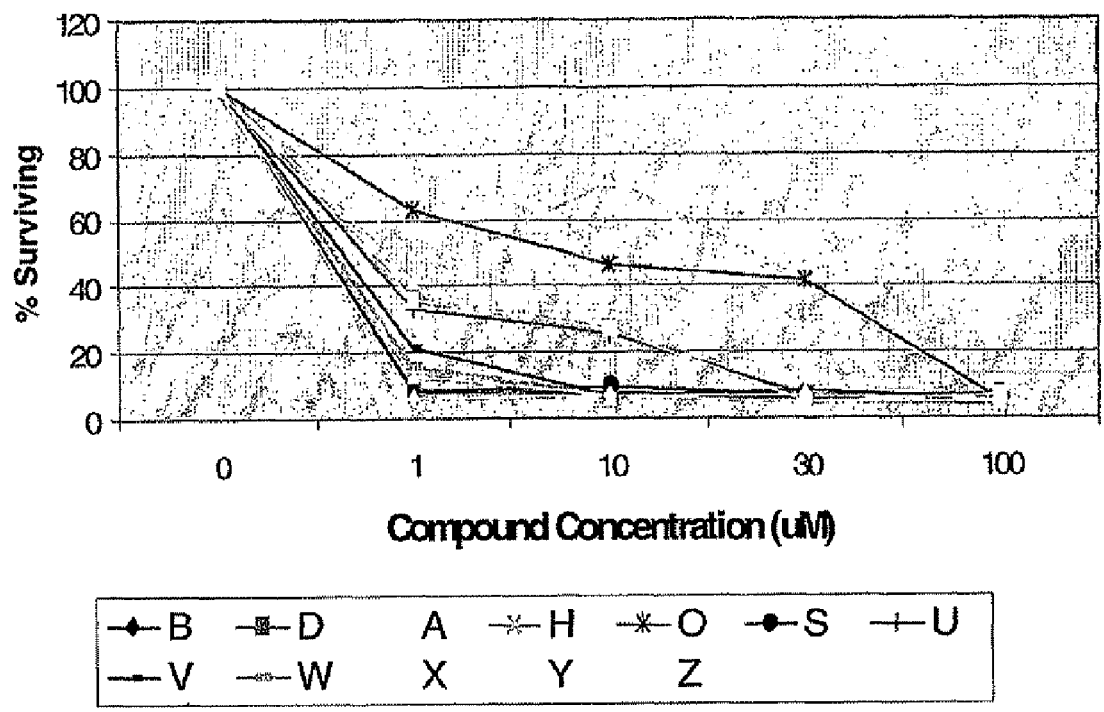
FIG. 2 is a graph showing a cytotoxicity screen of compounds on C6 cells. The compounds tested are designated by letter and are defined in the specification.
Figure 3:
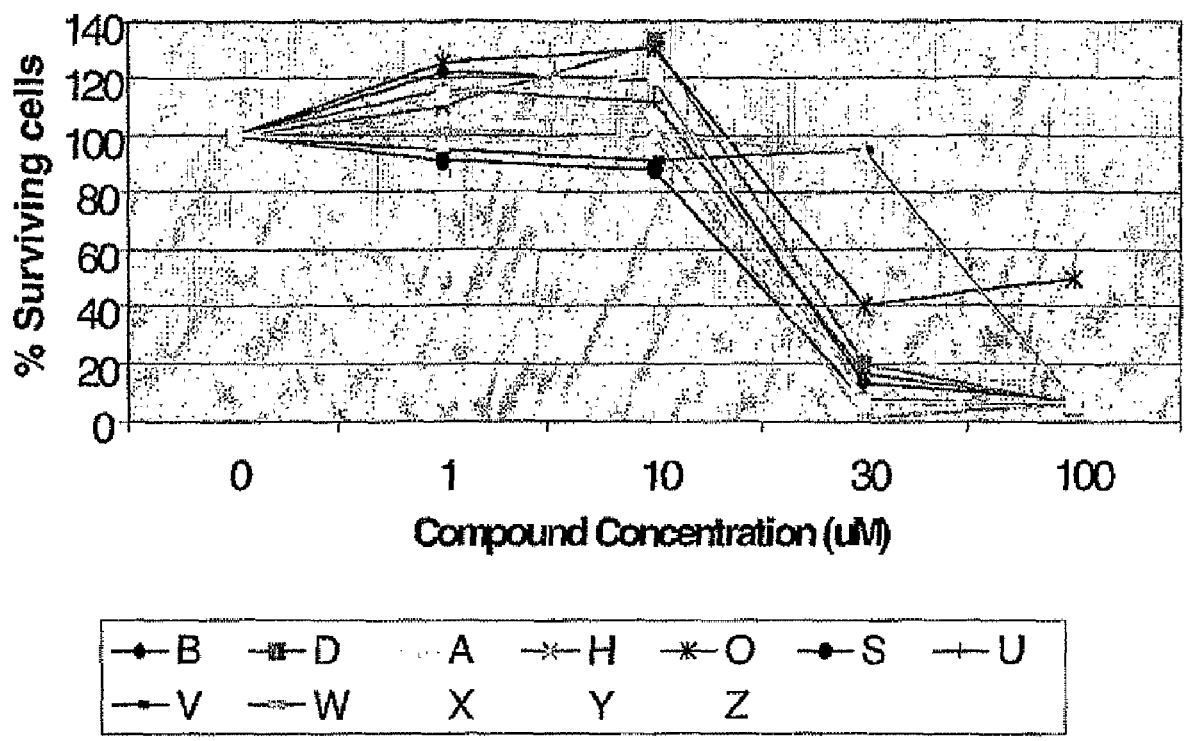
FIG. 3 is a graphical representation showing a cytotoxicity screen of different agents on U87MG cells. The compounds tested are designated by letter and are defined in the specification.

The compound of formula (I) is preferably a compound of formula (F):

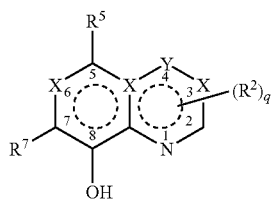

(I)' in which $R^2$ is H; optionally substituted $C_{1-4}$ alkyl; optionally substituted $C_{2-6}$ alkenyl; optionally substituted $C_{2-6}$ alkynyl; optionally substituted $C_{3-6}$ cycloalkyl; optionally substituted aryl; optionally substituted heterocyclyl; CN; $OR^6$, $SR^6$, $COR^6$, $CSR^6$, $HCNOR^6$ or $HCNNR^6$ in which $R^6$ is H, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl or optionally substituted heterocyclyl; $NR^8R^9$ or $SO_2NR^8R^9$ in which $R^8$ and $R^9$ are independently selected from H, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl and optionally substituted heterocyclyl; $CONR^9R^{10}$ in which $R^9$ is as defined above and $R^{10}$ is optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl or optionally substituted heterocyclyl; $CH_2CONR^8R^9$ in which $R^8$ and $R^9$ are as defined above; and $(CH_2)NR^9R^{11}$ in which $R^9$ is as defined above and $R^{11}$ is selected from optionally substituted $C_{1-6}$ alkyl, optionally substituted $C_{2-6}$ alkenyl, optionally substituted alkynyl, optionally substituted $C_{3-6}$ cycloalkyl, optionally substituted aryl, optionally substituted heterocyclyl and $SO_2R^{12}$ in which $R^{12}$ is optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl or optionally substituted heterocycyl and n is 1 to 6;

$R^5$ and $R^7$ are independently selected from H, optionally substituted $C_{1-6}$ alkyl and halo;

X is CH or N;

Y is CH, CO, CS or N; and q is 1, 2 or 3.

The compounds of formula (I') include those in which X and Y are CH; the X at the 3 position is N, the X at the 6 position is CH and the other X is CH and Y is CO or CS; the X at the 3 and 6 positions is CH and the other X is N and Y is CO; X is CH and Y is N; Y and X at position 3 are CH; X at position 6 is N and the other X is C.

In one embodiment, the compound of formula (I') has the formula (IA):

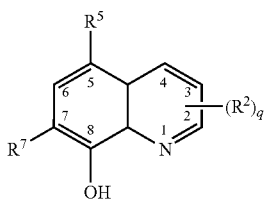

(IA)

in which $R^2$, $R^5$, $R^7$, $R^8$ and q are as defined above.

$R^2$ is preferably located at either the 2 or 3 positions or both and is selected from H; optionally substituted $C_{1-4}$ alkyl; optionally substituted $C_{2-4}$ alkenyl; optionally substituted $C_{3-6}$ cycloalkyl; optionally substituted 6-membered aryl optionally condensed with an optionally substituted 6 membered aryl or heteroaryl; optionally substituted saturated or unsaturated 5- or 6-membered N-containing heterocyclyl optionally condensed with an optionally substituted 6-membered aryl or heteroaryl; $(CH_2)_nR^{13}$ in which n is as defined above and $R^{13}$ is optionally substituted $C_{1-4}$ alkyl, optionally substituted $C_{3-6}$ cycloalkyl, optionally substituted saturated or unsaturated 5- or 6-membered N-containing heterocyclyl or optionally substituted 6-membered aryl; $NR^{14}R^{15}$ in which $R^{14}$ and $R^{15}$ are independently selected from H, optionally substituted $C_{1-4}$ alkyl, optionally substituted $C_{3-6}$ cycloalkyl, optionally substituted saturated or unsaturated 5- or 6-membered N-containing heterocyclyl and optionally substituted 6-membered aryl; $HCNOR^{16}$ in which $R^{16}$ is H, optionally substituted $C_{1-4}$ alkyl, optionally substituted $C_{3-6}$ cycloalkyl, optionally substituted membered saturated or unsaturated 5- or 6-N-containing heterocyclyl or optionally substituted 6-membered aryl; $CH_2CONR^{17}R^{18}$ in which $R^{17}$ and $R^{18}$ are independently selected from H, optionally substituted $C_{1-6}$ alkyl, optionally substituted $C_{2-6}$ alkenyl and optionally substituted 5 or 6-membered N-containing heterocyclyl optionally condensed with optionally substituted 6-membered aryl; and $(CH_2)_nNR^{19}R^{20}$ in which $R^{19}$ and $R^{20}$ are independently selected from optionally substituted $C_{1-6}$ alkyl, optionally substituted $C_{3-6}$ cycloalkyl and $SO_2R^{21}$ in which $R^{21}$ is selected from optionally substituted $C_{1-6}$ alkyl and optionally substituted 6-membered aryl and n is as defined above.

More preferably $R^2$ is H, optionally substituted $C_{1-4}$ alkyl or $(CH_2)_nNR^{19}R^{20}$ in which n, $R^{19}$ and $R^{20}$ are as defined above.

Preferably $R^5$ and $R^7$ are both halo, more preferably both are chloro or one is chloro and the other is iodo.

A subclass of compounds of formula (IA) have the formula (Ia):

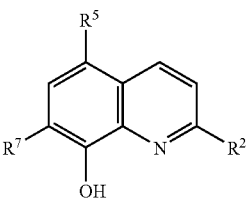

(Ia)

in which $R^2$, $R^5$ and $R^7$ are as defined above.

Subclasses of compounds of the formula (Ia) are as follows:

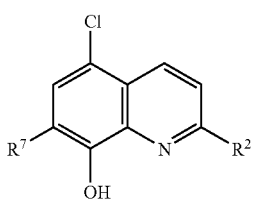

(i)

in which
R² is selected from H or optionally substituted saturated or unsaturated 6-membered N-containing heterocycyl such as pyridyl; and
R⁷ is Cl or I.

Representative examples are shown below:

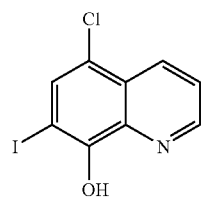
Compound A

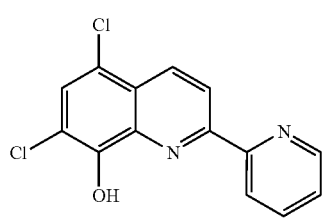
Compound ZA (ii)

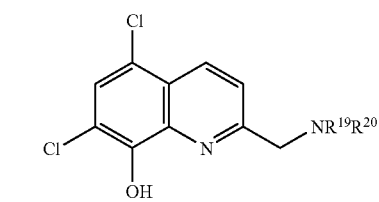

in which
R¹⁹ and R²⁰ are independently selected from H and optionally substituted $C_{1-6}$ alkyl.

Representative examples are shown below:

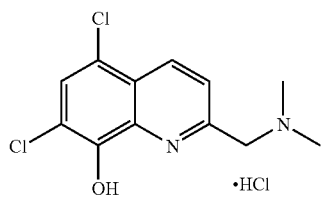
Compound B

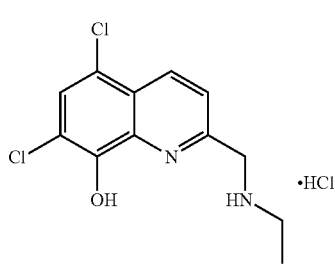
Compound D

-continued

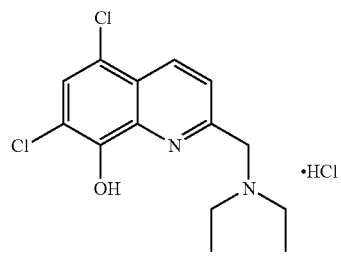
Compound G

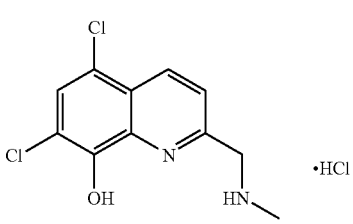
Compound J

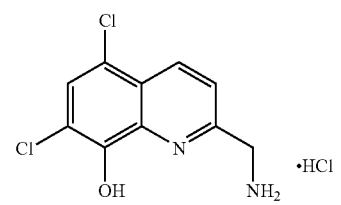
Compound K (iii)

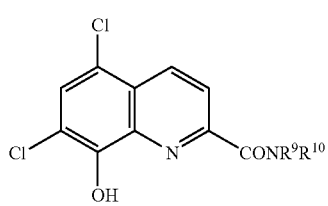

in which
R⁹ is H; and
R¹⁰ is selected from optionally substituted $C_{1-6}$ alkyl, more preferably $C_{1-6}$ alkyl optionally substituted with an unsaturated 5-membered N-containing heterocycyl such as an imidazolyl.

Representative examples are shown below:

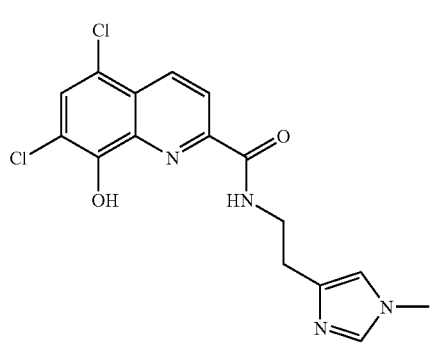
Compound C

Compound E

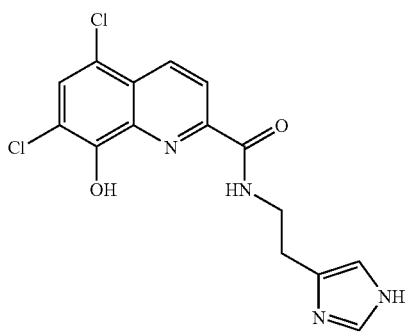

(iv)

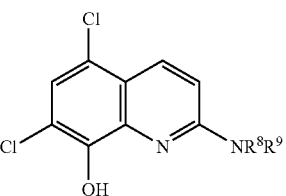

in which
$R^8$ and $R^9$ are independently selected from H, optionally substituted $C_{1-6}$ alkyl and an optionally substituted saturated or unsaturated 5- or 6-membered N-containing heterocyclyl such as pyridinyl.

A representative example is shown below:

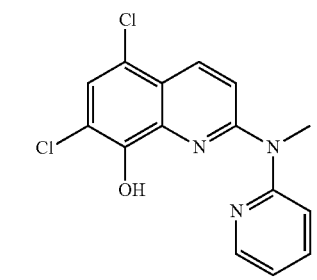

(v)

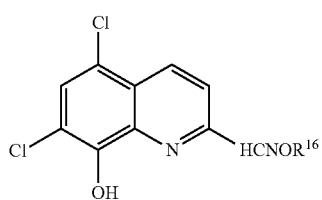

in which
$R^{16}$ is H or optionally substituted $C_{1-6}$, preferably $C_{1-4}$ alkyl.

Representative examples are shown below:

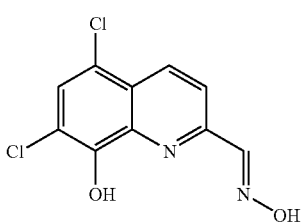

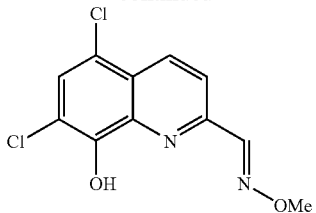

In another embodiment, the compound of formula (I') has the formula (IB):

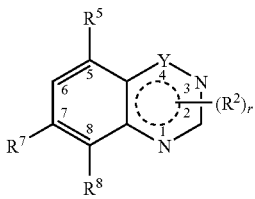

(IB)

in which
$R^2$, $R^5$, $R^7$, $R^8$ and Y are as defined above; and
r is 1 or 2.

$R^2$ is preferably located at either the 2 or 3 positions or both and is selected from H; optionally substituted $C_{1-4}$ alkyl; optionally substituted $C_{1-4}$ alkenyl; optionally substituted $C_{3-6}$ cycloalkyl; optionally substituted 6-membered aryl optionally condensed with an optionally substituted 6 membered aryl or heteroaryl; optionally substituted saturated or unsaturated 5- or 6-membered N-containing heterocyclyl optionally condensed with an optionally substituted 6-membered aryl or heteroaryl; $(CH_2)_n R^{13}$ in which n is as defined above and $R^{13}$ is optionally substituted $C_{1-4}$ alkyl, optionally substituted $C_{3-6}$ cycloalkyl, optionally substituted saturated or unsaturated 5- or 6-membered N-containing heterocyclyl or optionally substituted 6-membered aryl; $NR^{14}R^{18}$ in which $R^{14}$ and $R^{15}$ are independently selected from H, optionally substituted $C_{1-4}$ alkyl, optionally substituted $C_{3-6}$ cycloalkyl, optionally substituted saturated or unsaturated 5- or 6-membered N-containing heterocyclyl and optionally substituted 6-membered aryl; $NHCOR^{16}$ in which $R^{16}$ is optionally substituted $C_{1-4}$ alkyl, optionally substituted $C_{3-6}$ cycloalkyl, optionally substituted membered saturated or unsaturated 5- or 6-N-containing heterocyclyl or optionally substituted 6-membered aryl; $CH_2CONR^{17}R^{18}$ in which $R^{17}$ and $R^{18}$ are independently selected from H, optionally substituted $C_{1-6}$ alkyl, optionally substituted $C_{2-6}$ alkenyl and optionally substituted 5 or 6-membered N-containing heterocyclyl optionally condensed with optionally substituted 6-membered aryl; and $(CH_2)_n NR^{19}R^{20}$ in which $R^{19}$ and $R^{20}$ are independently selected from optionally substituted $C_{1-6}$ alkyl, optionally substituted $C_{3-6}$ cycloalkyl and $SO_2R^{21}$ in which $R^{21}$ is selected from optionally substituted $C_{1-6}$ alkyl and optionally substituted 6-membered aryl and n is as defined above, More preferably $R^2$ is selected from optionally substituted $C_{1-4}$ alkyl; optionally substituted $C_{1-4}$ alkenyl; an optionally substituted saturated or unsaturated 5- or 6-membered N-containing heterocyclyl optionally condensed with an optionally substituted 6-membered aryl or heteroaryl; $(CH_2)_n R^{13}$ in which n is 1 to 3 and $R^{13}$ is optionally substituted $C_{3-6}$ cycloalkyl or an optionally substituted saturated or unsaturated 5- or 6-membered N-containing heterocyclyl; $NR^{14}R^{15}$ in which $R^{14}$ is H and $R^{15}$ is H or optionally substituted $C_{1-4}$ alkyl or optionally substituted 6-membered aryl; NHCOR$^{16}$ in which R$^{16}$ is optionally substituted C$_{1-4}$ alkyl or optionally substituted 6-membered aryl.

Preferably R$^5$ is H or chloro and R$^7$ is chloro or iodo.

A subclass of compounds of formula (IB) have the formula (Ib)

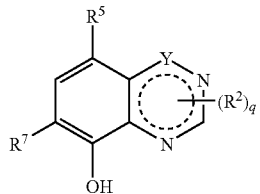

(Ib)

in which
R$^2$, R$^5$, R$^7$, Y and q are as defined above.

Subclasses of compounds of the formula (Ib) are as follows:

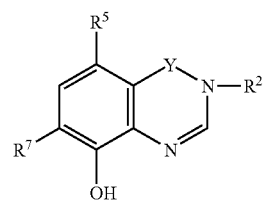

(i)

in which
R$^2$ is selected from optionally substituted C$_{1-6}$ alkyl and optionally substituted C$_{3-6}$ cycloalkyl;
R$^5$ is Cl or H;
R$^7$ is Cl or I; and
Y is CO or CS.

Representative examples are as follows:

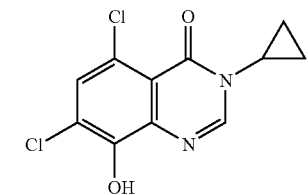

Compound F

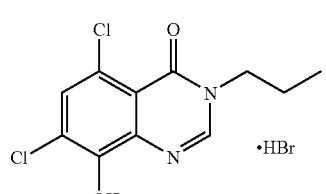

Compound P

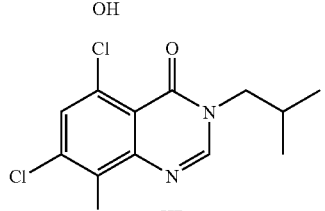

Compound R

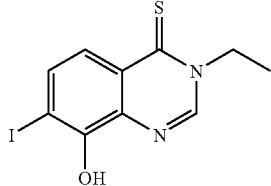

Compound Z

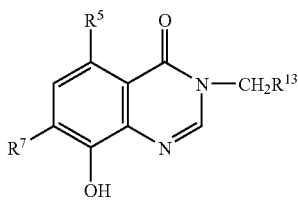

(ii)

in which
R$^5$ and R$^7$ are as defined above; and
R$^{13}$ is as defined above, preferably optionally substituted C$_{3-6}$cycloalkyl or optionally substituted 5- or 6-membered heterocyclyl such as pyridinyl, thiazolyl or isoxazolyl.

Representative examples are as follows:

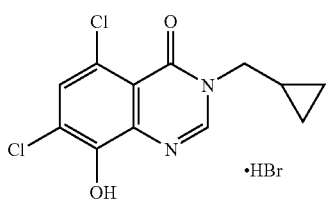

Compound H

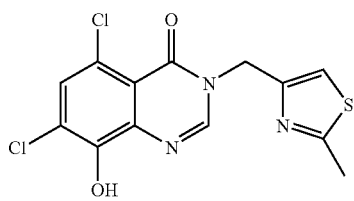

Compound I

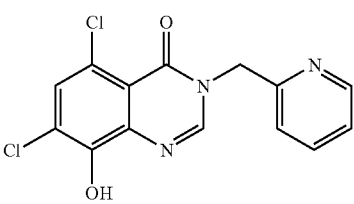

Compound N

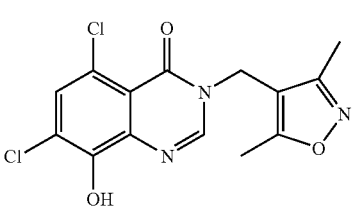

Compound O

-continued

Compound U

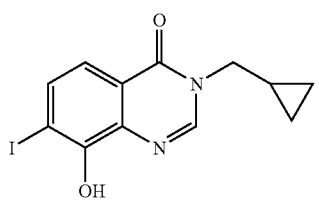

(iii)

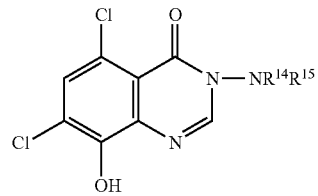

in which
$R^{14}$ and $R^{15}$ are as defined above, preferably independently selected from H and optionally substituted 6-membered aryl such as phenyl substituted with halo.

A representative example is as follows:

Compound Q

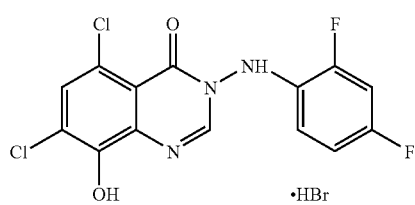

(iv)

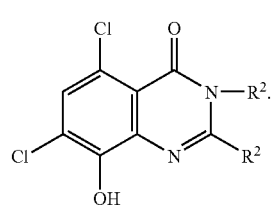

in which
$R^2$ is selected from optionally substituted $C_{1-6}$ alkyl, $CH_2NR^9R^{11}$ in which $R^9$ is H and $R^{11}$ is optionally substituted $C_{1-6}$ alkyl.

A representative example is shown below:

Compound T

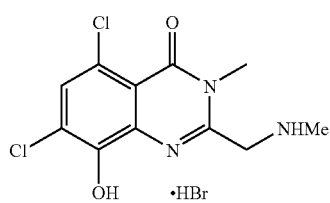

In another embodiment, the compound of formula (I') has the formula (IC):

(IC)

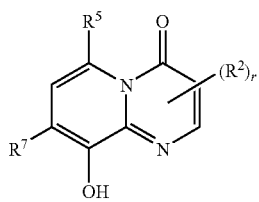

in which
$R^2$, $R^5$, $R^7$ and r are as defined above.
$R^2$ is preferably located at the 3 position and is selected from H, optionally substituted $C_{1-4}$ alkyl and $CONR^9R^{10}$ in which $R^9$ and $R^{10}$ are as defined above, preferably $R^8$ is H and $R^7$ is chloro or iodo.

A subclass of compounds of formula (IC) have the formula (Ic):

(Ic)

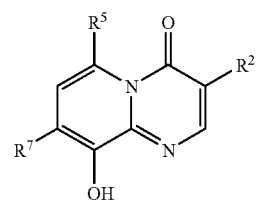

in which $R^2$, $R^5$ and $R^7$ are as defined above.

Subclasses of compounds of the formula (Ic) are as follows:

(i)

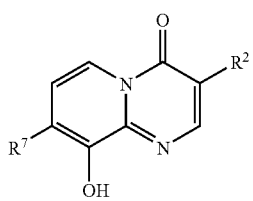

in which $R^2$ is optionally substituted $C_{1-6}$ alkyl; and $R^7$ is as defined above, preferably H or I.

Representative examples are shown below:

Compound V

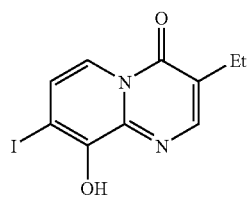

Compound W

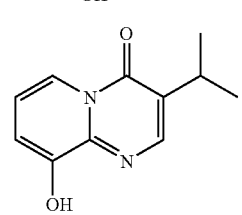

-continued

Compound X

Compound S (ii)

in which
R$^7$ is as defined above, preferably I;
R$^9$ is H; and
R$^{10}$ is optionally substituted C$_{1-6}$ alkyl.

A representative example is shown below:

Compound Y

In another embodiment, the compound of the formula (I') has the formula (ID):

(ID)

in which
R$^2$, R$^5$, R$^6$ and r are as defined above.

A subclass of compounds of the formula (ID) have the formula (Id):

(Id)

in which
R$^2$, R$^5$, R$^6$ and R$^7$ are as defined above.
R$^2$ is preferably optionally substituted C$_{1-6}$ alkyl and R$^5$ and R$^7$ are both chloro.

A representative example is as follows:

Compound M

In another embodiment, the compound of formula (I') has the formula (IE):

(IE)

in which
R$^2$, R$^5$ and q are as defined above.

A subclass of compounds of formula (IE) have the formula (Ie):

(Ie)

in which
R$^2$ is as defined above; and
R$^7$ is optionally substituted C$_{1-6}$ alkyl.

A representative example is as follows:

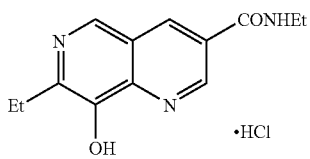

Compound L

·HCl

The terms "$C_{1-6}$ alkyl" or "$C_{1-4}$ alkyl" used either alone or in compound words such as "optionally substituted $C_{1-4}$ alkyl" refers to straight chain or branched chain hydrocarbon groups having from 1 to 6 and 1 to 4 carbon atoms, respectively. Illustrative of such alkyl groups are methyl, ethyl, propyl, isopropyl, butyl, isobutyl, sec-butyl, tert-butyl, pentyl, neopentyl or hexyl, preferably methyl, ethyl or propyl.

The term "$(CH_2)_n$" as used herein include both linear and branched chains.

The term "$C_{2-6}$ alkenyl" refers to straight chain or branched chain hydrocarbon groups having at least one double bond of either E or Z stereochemistry where applicable and 2 to 6 carbon atoms. Examples include vinyl, 1-propenyl, 1- and 2-butenyl and 2-methyl-2-propenyl.

The term "$C_{2-6}$ alkynyl" used either alone or in compound words such as "optionally substituted $C_{2-6}$ alkynyl" refers to straight chain or branched chain hydrocarbon groups having from 2 to 6 carbon atoms and having in addition one triple bond. Illustrative of such groups are ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

The term "$C_{3-6}$ cycloalkyl" used either alone or in compound words such as "optionally substituted $C_{3-6}$ cycloalkyl" refers to saturated carbocyclic groups having 3 to 6 carbon atoms. Illustrative of such groups are cyclopropyl, cyclobutyl, cyclopentyl and cyclohexyl, preferably cyclopropyl.

The term "heterocyclyl" refers to saturated or unsaturated, monocyclic or polycyclic hydrocarbon groups containing at least one heteroatom atom selected from the group consisting of nitrogen, sulphur and oxygen.

Suitable heterocyclic groups include N-containing heterocyclic groups, such as, unsaturated 5- or 6-membered heteromonocyclic groups containing 1 to 4 nitrogen atoms, for example, pyrrolyl, pyrrolinyl, imidazolyl, pyrazolyl, pyridyl, pyridinyl, pyrimidinyl, pyrazinyl, pyridazinyl, triazolyl or tetrazolyl;

saturated 5- or 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, benzimidazolyl, quinolyl, isoquinolyl, indazolyl, benzotriazolyl or tetrazolopyridazinyl;

unsaturated 5- or 6-membered heteromonocyclic group containing 1 to 2 oxygen atoms and 1 to 3 nitrogen atoms, such as, oxazolyl, isoxazolyl or oxadiazolyl;

saturated 5- or 6-membered heteromonocyclic group containing 1 to 2 oxygen atoms and 1 to 3 nitrogen atoms, such as, morpholinyl;

unsaturated 5- or 6-membered heteromonocyclic group containing 1 to 2 sulphur atoms and 1 to 3 nitrogen atoms, such as, thiazolyl or thiadiazolyl; and saturated 3 to 6-membered heteromonocyclic group containing 1 to 2 sulphur atoms and 1 to 3 nitrogen atoms, such as, thiazolidinyl.

Preferably the heterocyclyl is an unsaturated 5 or 6-membered heteromonocyclic group containing 1 to 3 nitrogen atoms such as pyrazolyl, pyridinyl, pyrimidinyl or imidazolyl; a saturated 5 or 6-membered heteromonocyclic group containing 1 to 4 nitrogen atoms such as pyrrolidinyl or piperazinyl; an unsaturated condensed heterocyclic group containing 1 to 5 nitrogen atoms such as benzimidazolyl; a saturated 5 or 6-membered heteromonocyclic group containing 1 to 2 oxygen atoms and 1 to 3 nitrogen atoms such as morpholinyl; or an unsaturated 5- or 6-membered heteromonocyclic group containing 1 to 2 sulphur atoms and 1 to 3 oxygen atoms, such as thiazolyl.

The term "unsaturated or saturated 5- or 6-membered N-containing heterocyclyl group optionally condensed with an optionally substituted 6-membered aryl" used either alone or in compound words such as "optionally substituted unsaturated or saturated 5- or 6-membered N-containing heterocyclyl group optionally condensed with an optionally substituted 6-membered aryl" refers to monocyclic or polycyclic heterocyclic groups containing at least one nitrogen atom and optionally other heteroatoms selected from sulphur and oxygen.

The term "aryl" refers to single, polynuclear, conjugated or fused residues of aromatic hydrocarbons. Examples include phenyl, biphenyl, terphenyl, quaterphenyl, naphthyl, tetrahydronaphthyl, anthracenyl, dihydroanthracenyl, benzanthracenyl, dibenxanthracenyl and phenanthrenyl. A preferred aryl is phenyl.

The term "6-membered aryl" used either alone or in compound words such as "optionally substituted 6-membered aryl" denotes a 6-membered carbocyclic aromatic group. Illustrative of such aryl groups are phenyl. Preferably, the aryl is optionally substituted phenyl such as 4-halophenyl, more preferably 4-fluorophenyl.

The term "6-membered heteroaryl" used either alone or in compound words such as "optionally substituted 6-membered hetroaryl" denotes a 6-membered aromatic heterocycle containing one or more heteroatoms. Examples include pyridyl pyrazinyl, pyrimidinyl and pyridazinyl, each of which may be optionally substituted by methyl or methoxy.

The term "halo" refers to fluorine, chlorine, bromine or iodine, preferably fluorine, iodine or chlorine, more preferably chlorine or iodine.

The term "acyl" used either alone or in compound words such as "optionally substituted acyl", "aryl acyl" or "alkyl acyl", denotes carbamoyl, aliphatic acyl group, acyl group containing an aromatic ring which is referred to as aromatic acyl or an acyl group containing a heterocyclic ring which is referred to as heterocyclic acyl having 1 to 20 carbon atoms, preferably 1 to 14 carbon atoms. Examples of acyl include carbamoyl; straight chain or branched alkanoyl, such as, formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl or icosanoyl; alkoxycarbonyl, such as, methoxycarbonyl, ethoxycarbonyl, t-butoxycarbonyl, t-pentyloxycarbonyl or heptyloxycarbonyl; cycloalkylcarbonyl, such as, cyclopropylcarbonyl, cyclobutylcarbonyl, cyclopentyl, carbonyl or cyclohexylcarbonyl; alkylsulfonyl, such as, methylsulfonyl or ethylsulfonyl; alkoxysulfonyl, such as, methoxysulfonyl or ethoxysulfonyl; aroyl, such as, benzoyl, toluoyl or naphthoyl; aralkanoyl, such as, phenylalkanoyl, for example, phenylacetyl, phenylpropanoyl, phenylbutanoyl, phenylisobutyl, phenylpentanoyl or phenylhexanoyl or naphthylalkanoyl, for example, naphtbylacetyl, naphthylpropanoyl or naphthylbutanoyl; aralkenoyl, such as, phenylalkenoyl, for example, phenylpropenoyl, phenylbutenoyl, phenylmethacrylyl, phenylpentenoyl or phenylhexenoyl or naphthylallcenoyl, for example, naphthylpropenoyl, naphthylbutenoyl or naphthylpentenoyl; aralkoxycarbonyl, such as, phenylalkoxycarbonyl, for example, benzyloxycarbonyl; aryloxycarbonyl, such as, phenoxycarbonyl or naphthyloxycarbonyl, aryloxyalkanoyl, such as, phenoxyacetyl or phenoxypropionyl, arylcarbamoyl, such as, phenylcarbamoyl; arylthiocarbamoyl, such as, phenylthiocarbamoyl, arylglyoxyloyl, such as, phenylglyoxyloyl or naphthylglyoxyloyl; arylsulfonyl, such as, phenylsulfonyl or naphthylsulfonyl; heterocycliccarbonyl; heterocyclicalkanoyl, such as, thienylacetyl, thienylpropanoyl, thienylbutanoyl, thienylpentanoyl, thienylhexanoyl, thiazolylacetyl, thiadiazolylacetyl or tetrazolylacetyl, heterocyclicalkenoyl, such as, heterocyclicpropenoyl, heterocyclicbutenoyl, heterocyclicpentenoyl or heterocyclichexenoyl; or heterocyclicglyoxyloyl, such as, thiazolylglyoxyloyl or thienylglyoxyloyl.

The term "optionally substituted thio" refers to optional substituents such as radicals containing a linear or branched alkyl of 1 to 10 carbon atoms, preferably 1 to 6 carbon atoms, more preferably 1 to 4 carbon atoms, attached to a divalent sulphur atom. Examples of alkylthio radicals include methylthio, ethylthio, propylthio, butylthio and hexylthio.

The term "optionally substituted sulfinyl" refers to optional substituents such as radicals containing a linear or branched alkyl radical, of 1 to 10 carbon atoms, preferably 1 to 6 carbon atoms, more preferably 1 to 4 carbon atoms, attached to a divalent —S(=O)— radical. Examples include methylsulfinyl, ethylsulfinyl, butylsulfinyl and hexylsulfinyl.

The term "optionally substituted sulfonyl" refers to optional substituents such as radicals containing a linear or branched alkyl radical of 1 to 10 carbon atoms, preferably 1 to 6 carbon atoms, more preferably 1 to 4 carbon atoms, attached to a divalent —$SO_2$— radical. Examples include methylsulfonyl, ethylsulfonyl and propylsulfonyl.

The term "alkoxy" refers to straight chain or branched oxy-containing radicals preferably each having alkyl portions of 1 to about 6 carbon atoms. Examples of alkoxy include methoxy, ethoxy, propoxy, butoxy and tert-butoxy.

The term "optionally substituted" refers to a group that may or may not be further substituted with one or more groups selected from $C_{1-6}$ alkyl, $C_{3-6}$ cycloalkyl, $C_{2-6}$ alkenyl, $C_{2-6}$ alkynyl, aryl, heterocyclyl, halo, halo$C_{1-6}$alkyl, halo$C_{3-6}$cycloalkyl, halo$C_{2-6}$alkenyl, halo$C_{2-6}$ alkynyl, haloaryl, haloheterocyclyl, hydroxy, $C_{1-6}$ alkoxy, $C_{2-6}$alkenyloxy, $C_{2-6}$alkynyloxy, aryloxy, heterocyclyloxy, carboxy, halo$C_{1-6}$alkoxy, halo$C_{2-6}$alkenyloxy, halo$C_{2-6}$alkynyloxy, haloaryloxy, nitro, nitro$C_{1-6}$alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclamino acyl, $C_{1-6}$alkylacyl, $C_{2-6}$alkenylacyl, $C_{2-6}$alkynylacyl, arylacyl, heterocycylylacyl, acylamino, acyloxy, aldehydro, $C_{1-6}$alkylsulphonyl, arylsulphonyl, $C_{1-6}$alkylsulphonylamino, arylsulphonylamino, $C_{1-6}$alkylsulphonyloxy, arylsulphonyloxy, $C_{1-6}$alkylsulphenyl, $C_{2-6}$alklysulphenyl, arylsulphenyl, carboalkoxy, carboaryloxy, mercapto, $C_{1-6}$alkylthio, arylthio, acylthio, cyano and the like. Preferably, the optional substituent is $C_{1-4}$ alkyl, halo $C_{1-4}$ alkyl, hydroxy, halo, $C_{1-4}$ alkoxy or $C_{1-4}$ alkylacyl.

Preferably the derivative is a "pharmaceutically acceptable derivative". By "pharmaceutically acceptable derivative" is meant any pharmaceutically acceptable salt, hydrate, ester, ether, amide, active metabolite, analogue, residue or any other compound which is not biologically or otherwise undesirable and induces the desired pharmacological and/or physiological effect.

The salts of the compounds of formula (I) are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethane, sulphonic, toluenesulphonic, benzenesulphonic, salicylic, sulphanilic, aspartic, glutamic, edetic, stearic, palmitic, oleic, lauric, pantothenic, tannic, ascorbic and valeric acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

In addition, some of the compounds of the present invention may form solvates with water or common organic solvents. Such solvates are encompassed within the scope of the invention.

The term "pro-drug" refers to functional derivatives of the compound of formula (I) which are readily convertible in vivo into the required compound of formula (I). Conventional procedures for the selection and preparation of suitable pro-drug derivatives are described, for example, in "Design of Prodrugs" ed. H. Bundgaard, Elsevier, 1985.

A prodrug may be a pharmacologically inactive derivative of the active compound that requires transformation within the body in order to release the active compound, and that has improved delivery properties over the active compound. The transformation in vivo may be, for example, as the result of some metabolic process, such as chemical or enzymatic hydrolysis of a carboxylic, phosphoric or sulphate ester, or reduction or oxidation of a susceptible functionality. In one embodiment, the 8-hydroxyl on the compounds of formula (I) may be blocked to form a prodrug, in particular an ester prodrug. The 8-hydroxy represents a principal site of metabolism for the compounds: conjugation with glucuronic acid or sulphate gives a hydrophilic species ready to be excreted.

The term "tautomer" is used herein in its broadest sense to include compounds of formula (I) which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereo isomers. As the compound of formula (I) may have one or more chiral centres, it is capable of existing in enantiomeric forms.

Included within the scope of this invention are compounds of the formula I to which at least one of a detectable label, an affinity tag and a photoreactive group is linked.

Methods of Treatment, Amelioration and/or Prophylaxis

Agents which comprise the compound of formula (I) may be used in the treatment, amelioration and/or prophylaxis of a glioma brain tumour such as astrocytoma, GBM and anaplastic astrocytoma, mixed glioma and oligodendroglioma.

Reference to an "agent" includes combinations of two or more active agents. A "combination" also includes multi-part such as a two-part composition where the agents are provided separately and given or dispensed separately or admixed together prior to dispensation. For example, a multi-part pharmaceutical pack may have two or more agents separately maintained. Hence, this aspect of the present invention includes combination therapy. Combination therapy includes the co-administration of an agent and another active such as a chemotherapeutic compound, a cytokine, genetic molecule and/or an anesthetic.

The terms "effective amount" and "therapeutically effective amount" of an agent as used herein mean a sufficient amount of the agent to provide the desired therapeutic or physiological or effect or outcome. Such an effect or outcome includes inhibiting the growth or viability of cells associated with a glioma in the brain. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

The effective amount is deemed the amount required to inhibit the growth or viability of cells associated with a glioma. Effective amounts include from about 1 ng to about 1 g/subject administration. The administration may be a single dose or a series of divided doses. Amounts include from about 5 ng to about 800 mg/subject administration. Actual amounts include about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 ng or 200, 300, 400, 500, 600, 700, 800, 900, 1000 ng or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg or 200, 300, 400, 500, 600, 700, 800, 900, 1000 mg per patient.

"Treating" a subject may involve modulating or ameliorating growth of a glioma brain tumour in an affected subject as well as treatment of a clinically a symptomatic subject having biochemical or immunological markers of a possible or developing glioma brain tumour, to the benefit of the subject. In one particular embodiment, the present invention contemplates a reduction of the growth or viability of cells associated with a glioma.

Reference to a "brain tumour" includes a brain cancer. The term "tumor" and "cancer" may be used interchangeably herein. Reference to a "glioma" includes GMB, astrocytoma, anaplastic astrocytoma, mixed glioma, oligodendroglioma or related brain cancers.

The "subject" as used herein refers to an animal, preferably a mammal and more preferably a primate including a lower primate and even more preferably a human who can benefit from the formulations and methods of the present invention. A subject regardless of whether a human or non-human animal may be referred to as an individual, patient, animal, host or recipient. The agents and methods of the present invention have applications in human medicine, veterinary medicine as well as in general, domestic or wild animal husbandry. For convenience, an "animal" includes an avian species such as a poultry bird (including ducks, chicken, turkeys and geese), an aviary bird or game bird. The condition in a non-human animal may not be a naturally occurring but induced such as in an animal model.

As indicated above, the preferred animals are humans, non-human primates such as marmosets, baboons, orangutan's, lower primates such as tupia, livestock animals, laboratory test animals, companion animals or captive wild animals. A human is the most preferred target. However, non-human animal models may be used.

Examples of laboratory test animals include mice, rats, rabbits, guinea pigs and hamsters. Rabbits and rodent animals, such as rats and mice, provide a convenient test system or animal model as do primates and lower primates. Livestock animals include sheep, cows, pigs, goats, horses and donkeys. Non-mammalian animals such as avian species, zebrafish, amphibians (including cane toads) and *Drosophila* species such as *Drosophila melanogaster* are also contemplated. Instead of a live animal model, a test system may also comprise a tissue culture system.

Pharmaceutical Formulations

The formulations of the present invention comprise at least one of the compounds of formula (I) together with one or more pharmaceutically acceptable carriers and optionally other therapeutic agents. Each carrier must be pharmaceutically "acceptable" in the sense of being compatible with the other ingredients of the formulations and not injurious to the subject. Carriers may include excipients and other additives such as diluents, detergents, coloring agents, wetting or emulsifying agents, pH buffering agents, preservatives, and the like. Formulations include those suitable for oral, rectal, nasal, topical (including buccal and sublingual), vaginal or parenteral (including subcutaneous, intramuscular, intravenous and intradermal) administration. The formulations may conveniently be presented in unit dosage form and may be prepared by methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers, diluents, adjuvants and/or excipients or finely divided solid carriers or both, and then if necessary shaping the product.

The compounds of formula (I) may be administered orally, topically, or parenterally in dosage unit formulations containing conventional non-toxic pharmaceutically acceptable carriers, adjuvants, and vehicles. The term parenteral as used herein includes subcutaneous injections, aerosol for administration to lungs or nasal cavity, intravenous, intramuscular, intrathecal, intracranial, injection, intraocular or infusion techniques.

The present invention also provides suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The formulations for oral use may contain one or more agents selected from the group of sweetening agents, flavoring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavoring agents include peppermint oil, oil of wintergreen, cherry, orange or raspberry flavoring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The above compounds as well as the pharmaceutically-active agent useful in the method of the invention can be administered, for in vivo application, parenterally by injection or by gradual perfusion over time independently or together. Administration may be intra-ocular, intravenously, intraarterial, intraperitoneally, intramuscularly, subcutaneously, intracavity, transdermally or infusion by, for example, osmotic pump. For in vitro studies the agents may be added or dissolved in an appropriate biologically acceptable buffer and added to a cell or tissue.

Preparations for, parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, attenuating agents, growth factors and inert gases and the like.

The present invention includes various pharmaceutical formulations useful for ameliorating disease. The pharmaceutical formulations according to one embodiment of the invention are prepared by bringing an above compound, analogs, derivatives or salts thereof, or combinations of the above compounds and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, attenuating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams and Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical formulations are adjusted according to routine skills in the art. See Goodman and Gilman's The Pharmacological Basis for Therapeutics (7th ed., 1985).

The pharmaceutical formulations are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical formulations according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, e.g., in Langer, *Science,* 249:1527, 1990.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical formulations may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The above compounds may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The above compounds may also be presented for use in the form of veterinary formulations, which may be prepared, for example, by methods that are conventional in the art. Examples of such veterinary formulations include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) intravaginally, e.g. as a pessary, cream or foam.

The present invention is further described by the following non-limiting Examples.

Example 1

Assessment of Compounds

The following Assays were used in the assessment of the compounds for suitability for use in the methods of the present invention.
Assay 1. Neurotoxicity Assays
Primary Cortical Neuronal Cultures Cortical cultures were prepared as previously described (White et al., *J Neuroscience* 18:6207-6217, 1998). Embryonic day 14 BL6Jx129sv mouse cortices were removed, dissected free of meninges and dissociated in 0.025% (wt/vol) trypsin. Dissociated cells were plated in 48 well culture plates at a density of $2 \times 10^6$ cells/mL in MEM with 25% (vol/vol) FCS and 5% (vol/vol) HS and incubated at 37° C., 2 hrs. Media was then replaced with Neurobasal media (Invitrogen Life Technologies) and B27 supplements (Invitrogen Life Technologies). Cultures were maintained at 37° C. in 5% $CO_2$. Prior to experimentation, the culture medium was replaced with Neurobasal media and B27 minus antioxidants (Invitrogen Life Technologies).
(a) MTS Assay for Cell Viability Cell viability is determined using the MTS assay. Culture medium is replaced with fresh neurobasal medium plus B27 supplements minus antioxidants. 1/10th volume MTS solution (Cell Titre 96 Aqueous One, Promega Corporation) and incubated at 37° C., 2 hrs. 200 microliter aliquots are measured with a spectrophotometer at 560 nm.
(b) Assay for Test Compound Cytoxicity Neuronal cortical cells were cultured for five days as per Assay 2 in NB media and B27 supplement.

On day six the test compounds were added to the neuronal cell cultures in NB media and B27 supplement minus antioxidants.

Test compounds were dissolved in 100% DMSO to a concentration of 2.5 mM (10 mM if excess compound was weighed out per vial—then diluted to 2.5 mM). 2.5 mM stock solution was serially diluted 1 in 10 to give working solutions of 250 μM, 25 μM, 2.5 μM. Test compounds were not added directly to cells, instead they were added to a 48 well 'Drug Plate' as comprised below:
Preparation of "Drug Plate":
To a 48 well plate add:
Well 1: 576 ul NB+B27 (no antioxidant)*+24 μl 2.5 μM test compound
Well 2: 576 ul NB+B27 (no antioxidant)+24 μl 25 μM test compound
Well 3: 576 ul NB+B27 (no antioxidant)+24 μl 250 μM test compound
Well 4: 576 ul NB+B27 (no antioxidant)+24 μl 2.5 μM test compound
Well 5: 576 ul NB+B27 (no antioxidant)+24 μl 25 μM test compound
Well 6: 576 ul NB+B27 (no antioxidant)+24 μl 250 μM test compound
Well 7: 576 ul NB+B27 (no antioxidant)+24 μl test compound diluent**
Well 8: 600 ul NB+B27 (no antioxidant)
*NB media and B27 (no antioxidants),
**PBT diluent 10% DMSO in NB+B27 (no antioxidants)

The Drug Plate was incubated at 37° C. for 15 mins. 200 μl of each well was added in triplicate to the corresponding cell plate. The cell plate was incubated at 37 C, for 4 days.

On completion of the assay, 1/10 volume MTS was added per well of plate (i.e. 25 μl/250 μl). The plates were incubated at 37 C for 2 hrs, and then absorbance was read at 560 nm.
Assay 2. Solubility Assay Stock solutions of test compounds (1 mM) were prepared in dimethyl sulfoxide. Compounds which did not dissolve were classed as not soluble (N). The DMSO stock solutions were diluted 1 in 100 into PBS pH 7.4. Compounds which gave a clear solution were classed as soluble (Y), while those compounds which gave a translucent suspension after dissolution in DMSO were classed as "crashed out" (C).
Assay 3. Physiochemical Properties
Polar Surface Area Calculations (PSA)

Polar surface area values were calculated using the web-based program available through "Molinspiration", a package for calculation of molecular properties.
Turbidimetric Solubility Measurements The solubility estimate was measured at both pH 2.0 and pH 6.5. This is within the pH range that can be anticipated along the proximal gastrointestinal tract in humans.

The compounds were dissolved in DMSO to appropriate concentrations and then spiked into either 0.01M HCl (approximately pH=2.0) or pH 6.5 isotonic phosphate buffer, the final DMSO concentration being 1%. Samples were then analysed via Nephelometry to determine a solubility range (Bevan and Lloyd, *Anal. Chem.* 72:1781-1787, 2000).
cLog P values Theoretical Log P values were determined using the ACD Log P software. The values quoted have been calculated from an untrained database and refer to the unionised species.

E Log D

Effective Log D values were measured using a chromatographic method employing a SUPELCOSIL LC-ABZ column using an octanol saturated mobile phase at pH 7.4. See F. Lombardo et al, J. Med. Chem. 2000, 43, 2922-2928.

Assay 4. Blood Brain Barrier Penetration

Each compound tested demonstrates a permeability across a healthy BBB.

A bolus injection of each of the test compound (50 µL of a 3 mg/mL aqueous solution containing 40% propylene glycol and 10% ethanol) was administered by tail vein injection to male Swiss Outbred mice (5-7 weeks of age).

At 5 and 60 min post-dose (n=3 mice at each time point), blood was collected by cardiac puncture and the whole brain was removed by making an incision through the back of the skull. Mice were anaesthetised approximately 3-4 min prior to blood and brain harvest with an intraperitoneal injection of ketamine and xylazine (133 mg/kg and 10 mg/kg, respectively).

The whole brain was placed into preweighed polypropylene vials and stored at −20° C. until analysis. On the day of analysis, the whole brain was homogenised in 3 parts of water (on ice to reduce the potential for ex vivo brain degradation) and an aliquot of the brain homogenate and plasma was analysed for compound concentration by LCMS. Standards were prepared by spiking blank brain homogenate and both samples and standards were processed by adding acetonitrile to the tissue homogenate, centrifuging and injecting an aliquot of the supernatant onto the LCMS.

To ensure complete recovery of compound from the brain, brain homogenate was spiked with compound (in 50% acetonitrile:50% water) to a nominal concentration of 500 ng/mL. The concentration of compound in the supernatant was then determined by LCMS and compared to the supernatant concentration when compound was added following precipitation with acetonitrile.

Calculations $$C_{brain} = C_{brain\ homogenate} - C_{brain\ vasculature}$$
$$C_{brain\ vasculature} = C_{plasma} * V_p$$
$$B:P = \frac{C_{brain}}{C_{plasma}}$$
$$P_{app}(cm/s) = \frac{C_{brain}}{\int_{-0}^{t} C_{plasma} \cdot dt * A}$$

$C_{brain}$=concentration of compound in brain parenchyma (ng/g)
$C_{brain\ homogenate}$=concentration of compound in brain homogenate (ng/g)
$C_{brain\ vasculature}$=concentration of compound in brain vasculature (ng/g)
$C_{plasma}$=concentration of compound in plasma (ng/mL)
$V_p$=brain plasma volume (26 µL/g for male Swiss Outbred mice)
B:P=brain-to-plasma ratio
$P_{app}$=apparent permeability coefficient of compound permeating the blood-brain barrier
$\int_0^t c_{plasma} \cdot dt$=concentration of compound in plasma from time zero to 5 min post-dose (equivalent to the 5 min post-dose plasma concentration, assuming no back diffusion from brain to plasma within this time period)
A=surface area of capillaries forming the blood-brain barrier (240 cm$^2$/g brain weight for mouse)

The brain and plasma concentrations of compounds following N administration to male Swiss Outbred mice at a nominal dose of 5 mg/kg is shown in FIG. 1. Each compound tested demonstrates a level of permeability across a healthy BBB.

Example 2

Properties of Compounds

The following table provides the properties and structures of compounds of the present invention.

| | | | In vivo Efficacy and Safety Profile | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 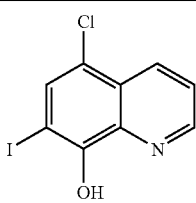 | Neuronal cells: 90, 77 M17 cells: 106.6, 72.7 | 305.5 33.1 | 4.32 (E) 1.85 (C) 2.17 | none | Up to 700 ng/mL | 0.20 at 5 min, 0.17 at 60 min |
| 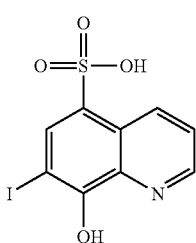 | Neuronal cells 70, 71 | 351.12 | 0.19 | | | |

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 5-amino-8-hydroxyquinoline dihydrochloride | Neuronal cells: 108, 71 | 233.10 | 1.53 | | | |
| 5,7-dichloro-8-hydroxyquinoline | Neuronal cells: 98, 75 | 214.05 | 3.34 | | | |
| 5,7-diiodo-8-hydroxyquinoline | Neuronal cells: 91, 95 | 396.96 | 4.14 | | | |
| 5,7-dibromo-8-hydroxyquinoline | Neuronal cells: 100, 94 | 302.95 | 3.69 | | | |
| 5-chloro-8-hydroxyquinoline | Neuronal cells: 94, 85 | 179.61 | 2.91 | | | |
| 8-hydroxy-2-methylquinoline | Neuronal cells 98, 58 | 159.19 | 2.58 | | | |
| 8-hydroxyquinoline-2-sulfonic acid | | 243.24 | −0.71 | | | |

-continued
| | In vivo Efficacy and Safety Profile | | | | |
|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 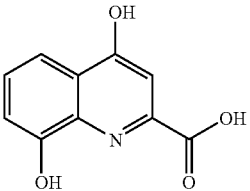 | | 205.17 | 3.00 | | | |
| 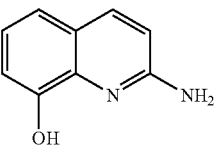 | Neuronal cells 95, 48 | 160.18 | 1.75 | | | |
| 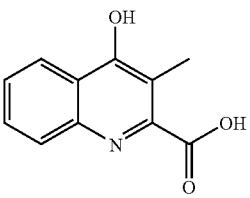 | | 189.17 | | | | |
| 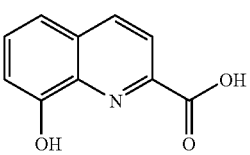 | | 189.17 | 2.67 | | | |
| 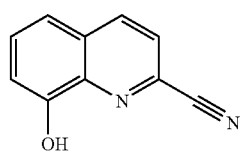 | Neuronal cells 94, 97 | 170.17 | 1.95 | | | |
| 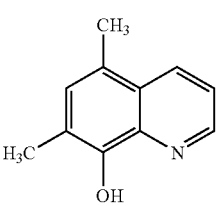 | Neuronal cells: 86, 85 | 173.22 | 3.03 | | | |
| 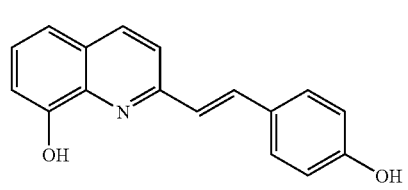 | Neuronal cells: 100, 75 | 263.30 | 3.70 | | | |
| 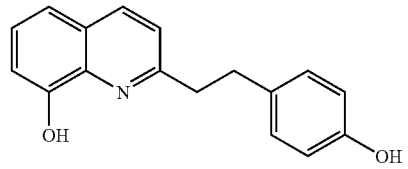 | Neuronal cells 89, 86 | 265.31 | 3.86 | | | |

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| [structure: 8-hydroxyquinoline-2-carboxamide with 3,5-di-tert-butyl-4-hydroxybenzyl] | | 406.53 | 6.67 | | | |
| [structure: 7-bromo-5-phenyl-8-hydroxyquinoline] | Neuronal cells: 100, 97 | 300.16 | 4.67 | | | |
| [structure: 5-chloro-7-phenyl-8-hydroxyquinoline] | Neuronal cells 93, 72 | 255.71 | 4.30 | | | |
| [structure: 5,7-diphenyl-8-hydroxyquinoline] | Neuronal cells: 97, 26 | 297.36 | 5.35 | | | |
| [structure: 5-chloro-7-(3-methoxyphenyl)-8-hydroxyquinoline] | Neuronal cells 83, 71 | 285.73 | 4.23 | | | |

-continued
| | In vivo Efficacy and Safety Profile | | | | | |
|---|---|---|---|---|---|---|
| Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] | |
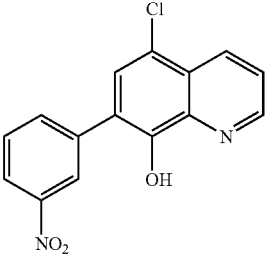
Neuronal cells 92, 78 | 300.70 | 4.06
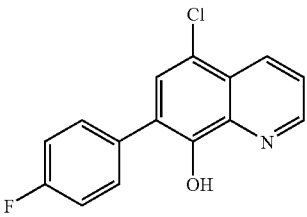
Neuronal cells 103, 75 | 273.70 | 4.45
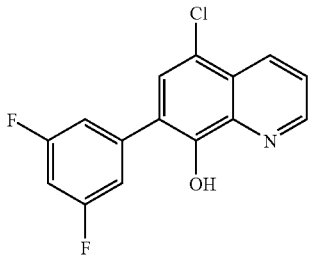
Neuronal cells 90, 66 | 291.69 | 4.60
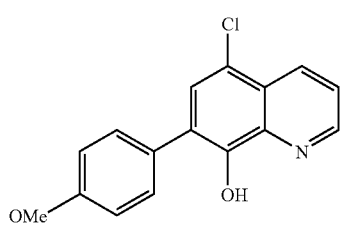
Neuronal cells 97, 31 | 285.73 | 4.23
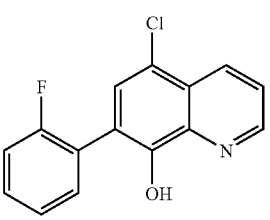
Neuronal cells 96, 54 | 273.70 | 4.45
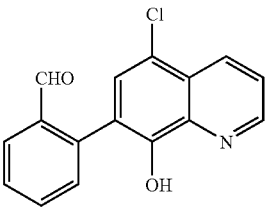
Neuronal cells 109, 99 | 283.72 | 3.67

-continued
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| 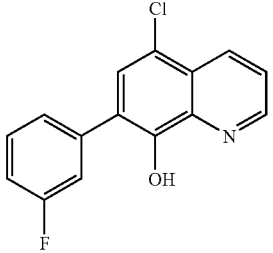 | Neuronal cells 98, 71 | 273.70 | 4.45 | | | |
| 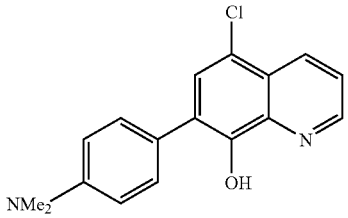 | Neuronal cells 94, 85 | 298.77 | 4.50 | | | |
| 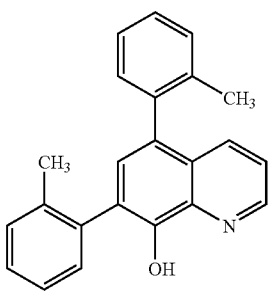 | Neuronal cells 93, 34 | 325.41 | 5.75 | | | |
| 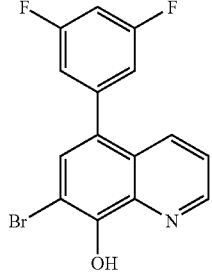 | Neuronal cells 95, 95 | 336.14 | 4.97 | | | |
| 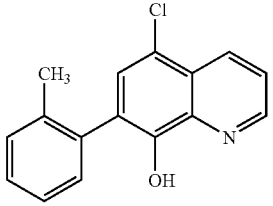 | Neuronal cells 100, 100 | 269.73 | 4.50 | | | |

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 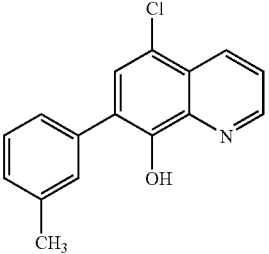 | Neuronal cells 98, 73 | 269.73 | 4.80 | | | |
| 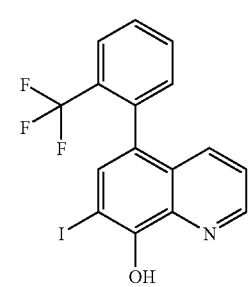 | Neuronal cells 91, 90 | 415.16 | 5.76 | | | |
| 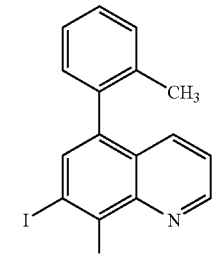 | Neuronal cells 99, 38 | 361.18 | 5.06 | | | |
| 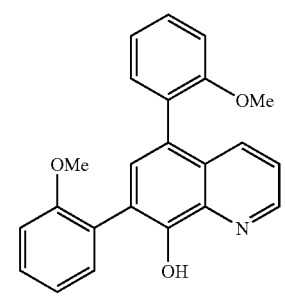 | Neuronal cells 100, 52 | 357.41 | 4.09 | | | |
| 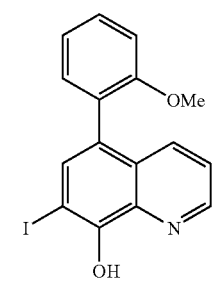 | Neuronal cells 91, 35 | 377.18 | 4.23 | | | |

-continued
| | In vivo Efficacy and Safety Profile | | | | |
|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 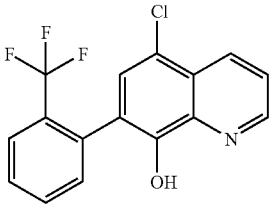 | Neuronal cells 96, 93 | 323.70 | 5.20 | | | |
| 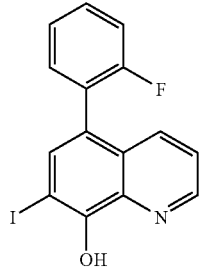 | Neuronal cells 92, 34 | 365.15 | 5.01 | | | |
| 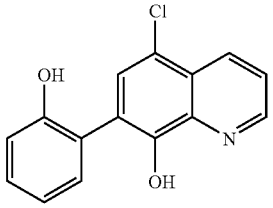 | Neuronal cells 100, 70 | 271.71 | 3.14 | | | |
| 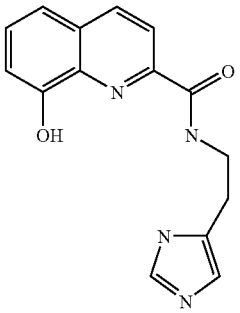 | Neuronal cells 100, 100 | 282.30 | 1.61 | | | |
| 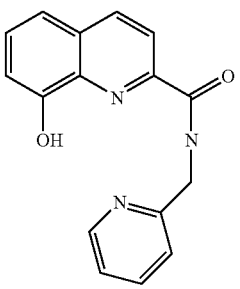 | Neuronal cells 96, 85 | 279.30 | 2.38 | | | |

-continued
| | In vivo Efficacy and Safety Profile | | | | |
|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
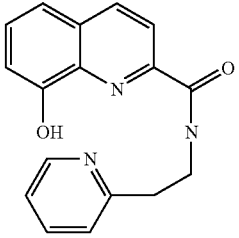
Neuronal cells 95, 93 — 293.33 — 2.51
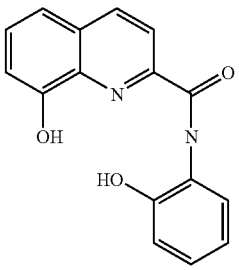
Neuronal cells 104, 92 — 280.29 — 3.26
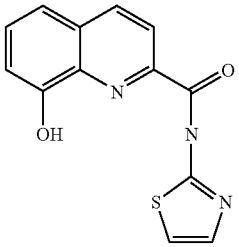
Neuronal cells 100, 100 — 271.30 — 2.47
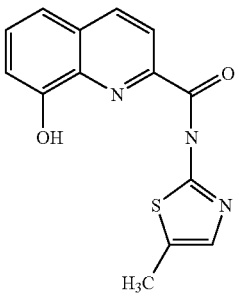
Neuronal cells 94, 68 — 285.33 — 2.93
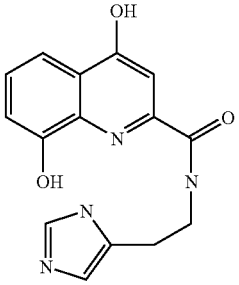
Neuronal cells 100, 100 — 298.30 — 1.70

-continued
| | In vivo Efficacy and Safety Profile | | | | |
|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
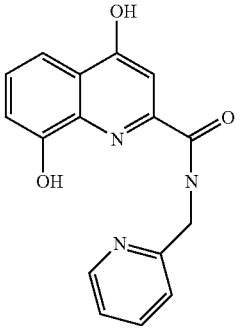
Neuronal cells 100, 100 — 295.30 — 2.71
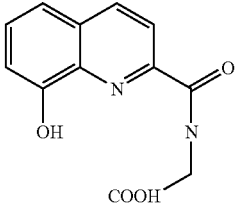
Neuronal cells 100, 89 — 246.22 — 1.70
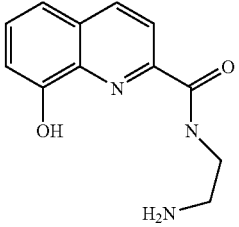
Neuronal cells 106, 96 — 231.26 — 1.43
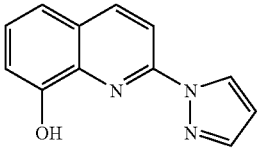
211.23 — 2.97
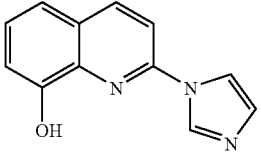
211.23 — 1.94
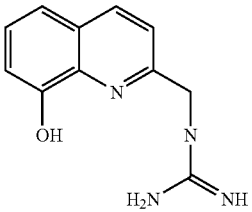
Neuronal cells 100, 89 — 216.24 — 0.20

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 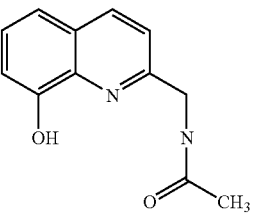 | Neuronal cells 100, 91 | 216.24 | 0.89 | | | |
| 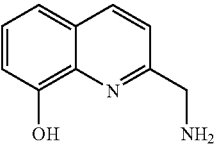 | Neuronal cells 101, 97 | 174.20 | 1.03 | | | |
| 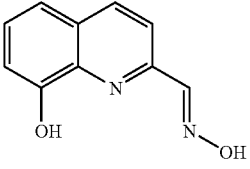 | Neuronal cells 100, 95 | 188.19 | 2.83 | | | |
| 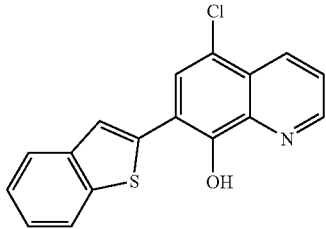 | Neuronal cells 87, 32 | 311.79 | 5.55 | | | |
| 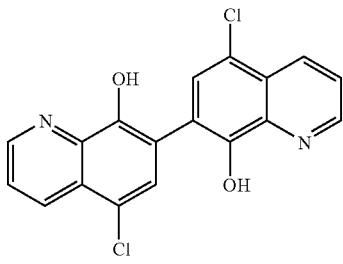 | Neuronal cells 97, 84 | 357.2 | 4.57 | | | |
| 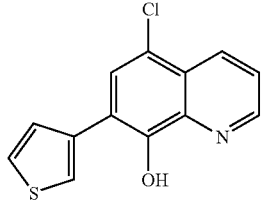 | Neuronal cells 93, 31 | 261.73 | 3.95 | | | |

-continued
|  | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
In vivo Efficacy and Safety Profile
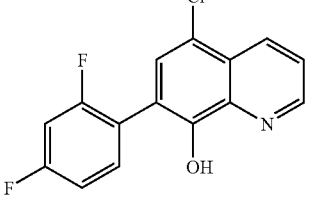
Neuronal cells 90, 42 | 291.69 | 4.60
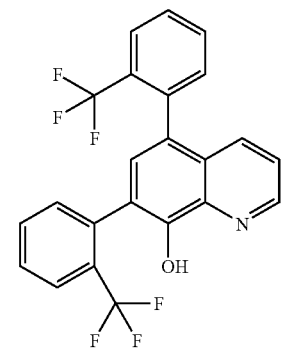
433.36 | 7.17
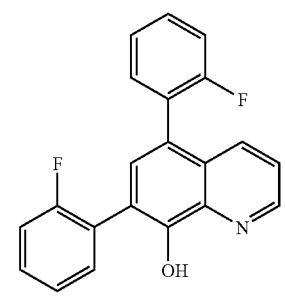
333.34 | 5.67
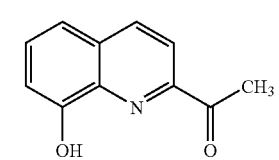
187.20 | 2.35
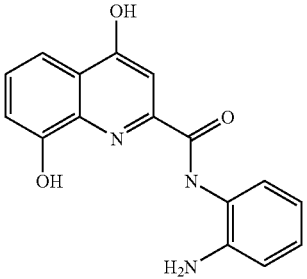
Neuronal cells 98, 82 | 295.30 | 2.80

-continued
| | In vivo Efficacy and Safety Profile | | | | |
|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 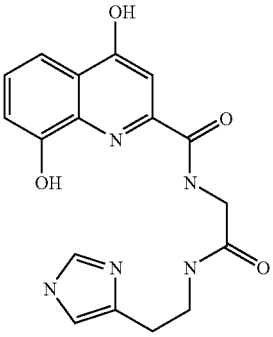 | Neuronal cells 98, 89 | 355.36 | 1.08 | | | |
| 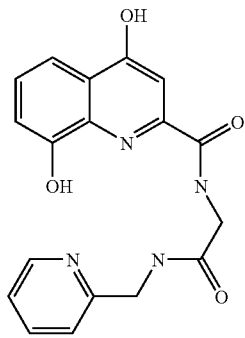 | Neuronal cells 93, 93 | 352.35 | 1.76 | | | |
| 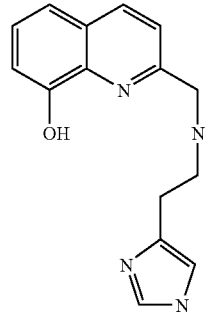 | Neuronal cells 101, 43 | 268.32 | 1.14 | | | |
| 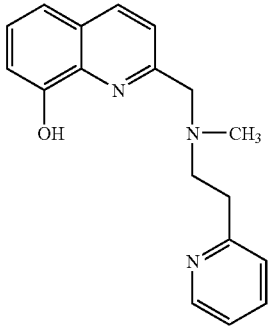 | Neuronal cells 97, 57 | 293.37 | 2.51 | | | |

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 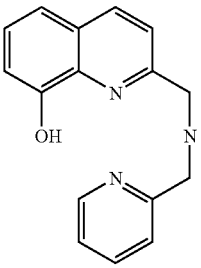 | Neuronal cells 96, 67 | 265.32 | 1.11 | | | |
| 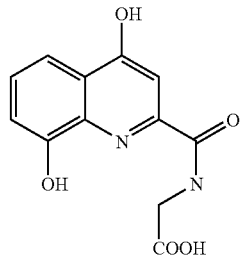 | Neuronal cells 98, 94 | 262.22 | 2.03 | | | |
| 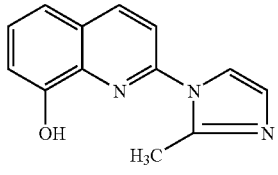 | Neuronal cells 104, 96 | 225.25 | 2.21 | | | |
| 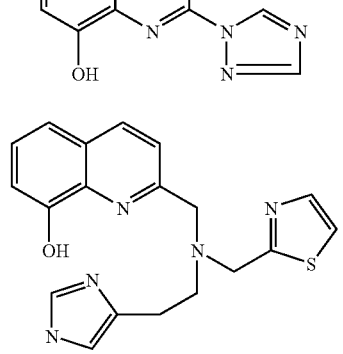 | Neuronal cells 102, 97 | 212.21 | 1.75 | | | |
| 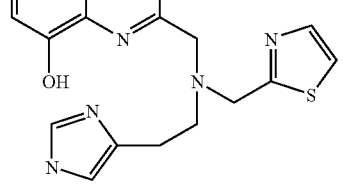 | Neuronal cells 82, 34 | 365.46 | 1.95 | | | |
| 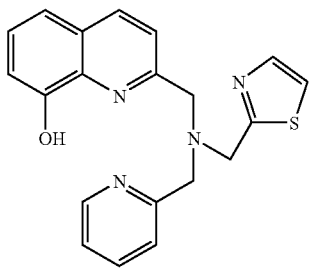 | Neuronal cells 97, 38 | 362.46 | 2.19 | | | |

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 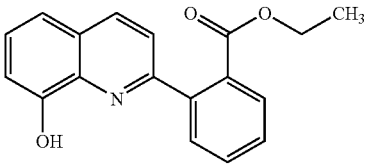 | | 293.33 | 4.70 | | | |
| 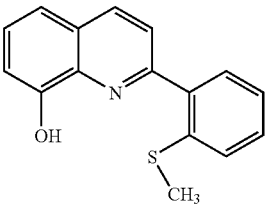 | Neuronal cells 114, 112 | 267.35 | 4.77 | | | |
| 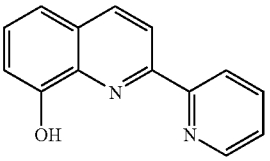 | Neuronal cells 107, 75 | 222.25 | 3.00 | | | |
| 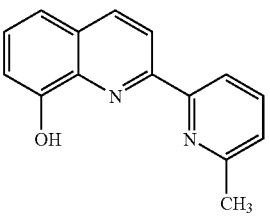 | Neuronal cells 91, 58 | 236.28 | 3.50 | | | |
| 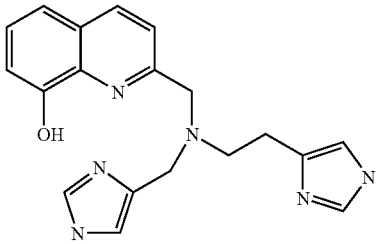 | Neuronal cells 97, 26 | 348.41 | 1.20 | | | |
| 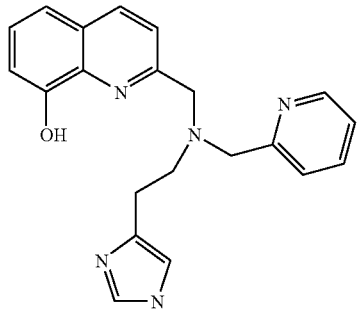 | Neuronal cells 98, 27 | 359.43 | 1.88 | | | |

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| (structure) | Neuronal cells 87, 23 | 356.43 | 2.35 | | | |
| (structure) | Neuronal cells 90, 70 | 345.41 | 1.68 | | | |
| (structure) | | 285.33 | 2.22 | | | |
| (structure) | Neuronal cells 81, 79 | 370.41 | 1.94 | | | |
| (structure) | Neuronal cells 93, 89 | 202.21 | 0.89 | | | |

-continued
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| 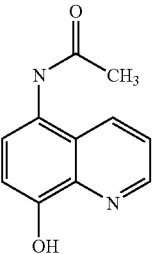 | | 202.21 | 1.72 | | | |
| 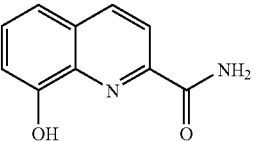 | | 188.19 | 1.60 | | | |
| 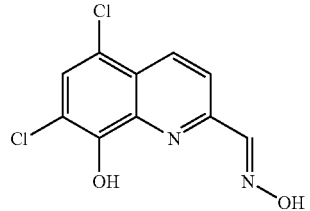 | Neuronal cells 91, 70 | 257.08 | 4.10 | | | |
| 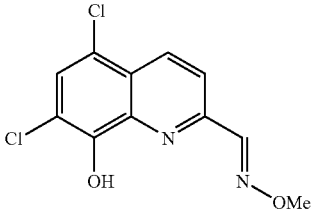 | Neuronal cells 77, 54 | 271.10 | 3.27 | | | |
| 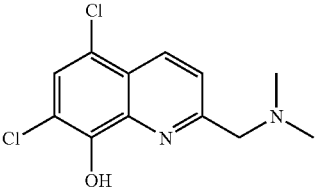 | Neuronal cells: 84, 72 M17 cells: 94, 54.3 | 271.1 36.36 | 3.51 (C) 1.07 | None | Up to 500 ng/ml | 12.85 at 5 min, 9.45 at 60 min |
| 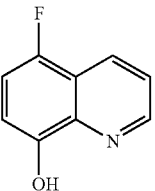 | | 163.15 | 2.34 | | | |

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| *[structure: 8-hydroxyquinoline-2-sulfonamide with imidazolyl ethyl]* | | 318.36 | 1.75 | | | |
| *[structure: 5-bromo-8-hydroxyquinoline-2-carboxamide with imidazolyl ethyl]* | | 361.20 | 2.54 | | | |
| *[structure: 5,7-dichloro-8-hydroxyquinoline-2-carboxamide]* | Neuronal cells 74, 86 | 257.08 | 2.78 | | | |
| *[structure: 5,7-dichloro-8-hydroxyquinoline-2-carboxamide with imidazolyl ethyl]* | Neuronal cells 91, 84 | 351.19 | 2.79 | | Up to 2694 ng/mL | |
| *[structure: 5,7-dichloro-8-hydroxyquinoline-2-carboxylic acid]* | Neuronal cells 88, 80 | 258.06 | 3.84 | | | |

-continued
| | | | In vivo Efficacy and Safety Profile | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 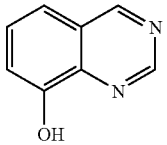 | | 146.15 | | | | |
| 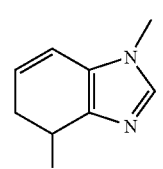 | | 180.25 | | | | |
| 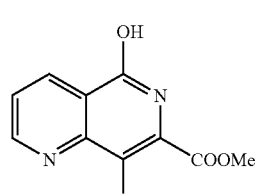 | | 220.19 | | | | |
| 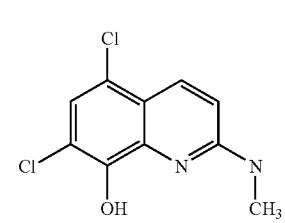 | | 243.09 | 3.82 | | | |
| 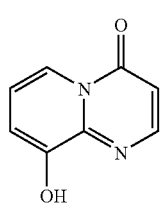 | | 162.15 | | | | |
| 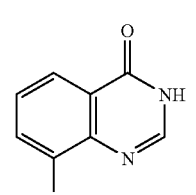 | Neuronal cells: 101, 89 | | | | | |
| 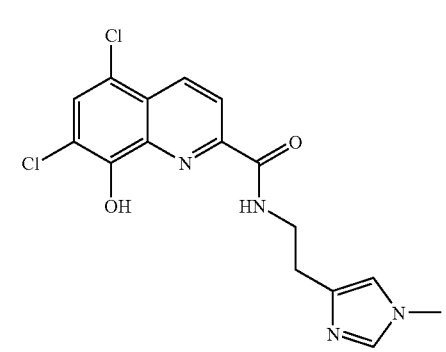 | Neuronal cells: 93, 88 M17 cells: 108.3, 82.6 | 365.2 80 | 2.56 | 10 days, none | Up to 11605 ng/mL | 0.06 at 5 min, 0.20 at 60 min |

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 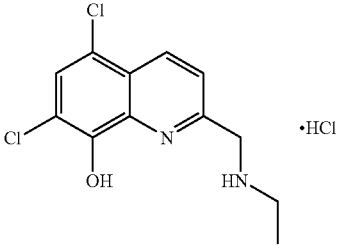 | Neuronal cells: 87, 56 M17 cells: 78.3, 44 | 307.6 44.6 | 3.58 | 10 days, none | Up to 403 ng/mL | |
| 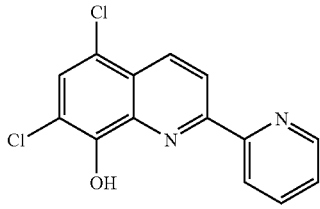 | Neuronal cells: 55, 31 | 291.14 | 4.21 | | | |
| 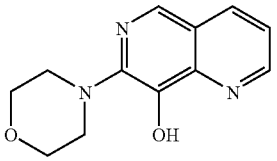 | Neuronal cells: 104, 98 M17 cells: 112, 93.7 | 231.3 58. | 1.99 (E) 1.45 | 10 days, mild toxic signs | Below 80 ng/mL in Tg mice | |
| 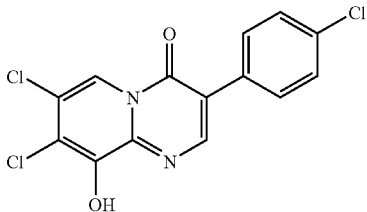 | | 341.58 | | | | |
| 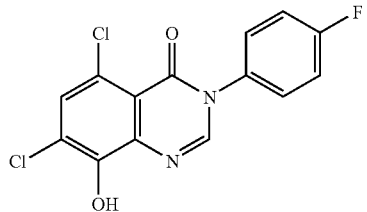 | Neuronal cells: 98, 67 M17 cells 93.2, 47.3 | 325.1 52.9 | 3.33 (E) 5.32 | 5 days, none | Up to 120 ng/mL in Tg mice | |
| 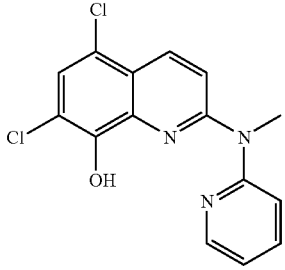 | Neuronal cells: 100, 59 | 320.18 | 4.51 | | | |

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 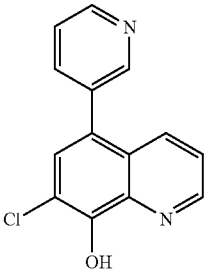 | Neuronal cells: 101, 84 | 256.69 | 3.00 | | | |
| 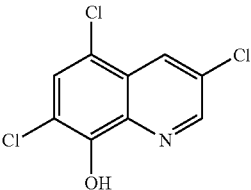 | Neuronal cells: 82, 55 | 248.50 | 4.07 | | | |
| 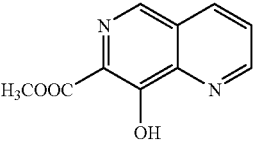 | | 204.19 | 1.48 | | | |
| 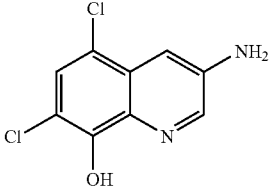 | Neuronal cells: 94, 10 | 229.07 | 3.02 | | | |
| 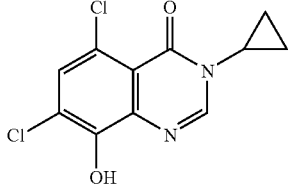 | Neuronal cells: 91, 77 M17 cells 105.3, 72 | 271.1 52.9 | 2.11 (C) 1.33 (C)$_{2.0}$ 1.41 | 10 days, none | Up to 5000 ng/mL | 0.26 at 5 min, 0.24 at 60 min |
| 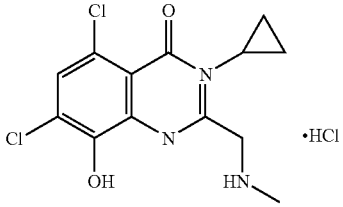 | | 330.22 | 1.49 | | | |
| 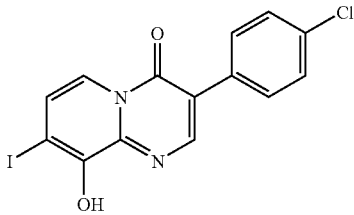 | Neuronal cells: 41, 33 | 398.6 52.9 | 3.41 | 10 days, mild toxic signs | Up to 450 ng/mL | |

-continued
| | In vivo Efficacy and Safety Profile | | | | |
|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
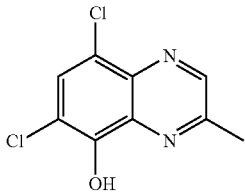
Neuronal cells: 100, 93 — 229.1 — 3.24
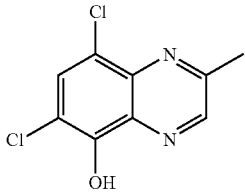
Neuronal cells: 94, 87 — 229.1 — 3.24
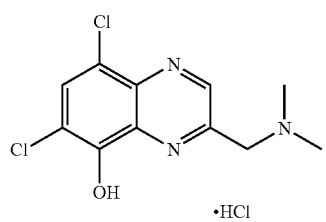
Neuronal cells: 106, 93 — 272.1 / 49.3 — 2.57 (C) 0.37 — Up to 1000 ng/mL
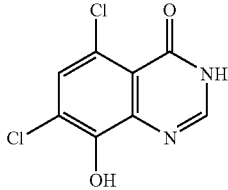
Neuronal cells: 100, 93 — 231.0 / 61.7 — 1.66 (C) 0.84 — 3 days, none — Below 100 ng/mL (single dose)
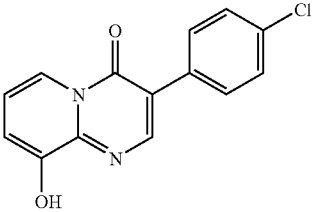
Neuronal cells: 97, 42 M17 cells: 41.2, 25.8 — 272.7 — 2.62
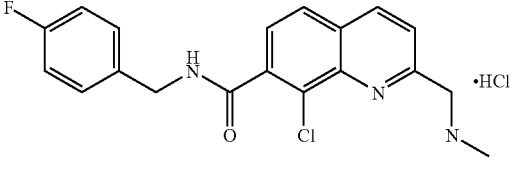
340.35 — 3.49
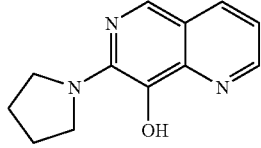
215.25 — 2.97

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 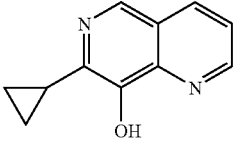 | Neuronal cells: 100, 98 | 186.1 46.0 | 2.22 | 6 days, none | Up to 350 ng/mL (single dose) | |
| 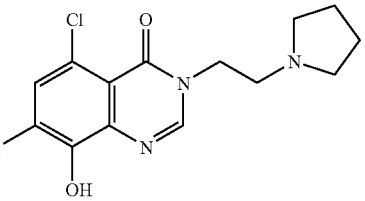 | Neuronal cells: 104, 91 M17 cells: 103.6, 101.3 | 328.2 58.4 | 2.58 | 14 days, 1 of 4 death | Up to 520 ng/mL (single dose) | |
| 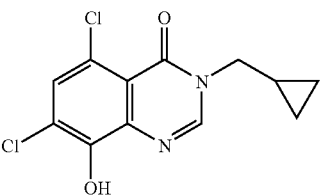 | Neuronal cells: 116, 105 M17 cells 96.2, 76.8 | 285.1 52.9 | 2.74 | 11 days, none | Up to 2698 ng/mL | 0.12 at 5 min, 0.07 at 60 min |
| 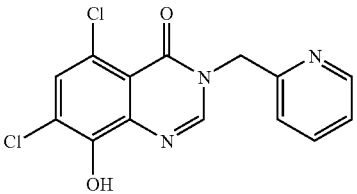 | Neuronal cells: 99, 98 M17 cells 101.9, 98.9 | 322.2 65.79 | 2.03 | 10 days, none | Up to 984 ng/mL | 0.16 at 5 min, 0.10 at 60 min |
| 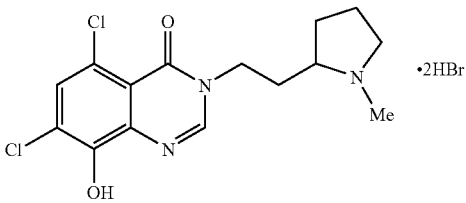 | Neuronal cells: 105, 94 | 342.2 58.4 | 2.87 | 10 days, none | Up to 262 ng/mL in mice (single dose) | |
| 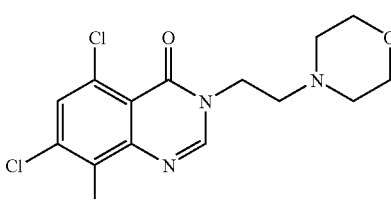 | Neuronal cells: 98, 81 | 344.2 67.6 | 1.92 | 10 days, none | Up to 10 ng/mL (single dose) | |
| 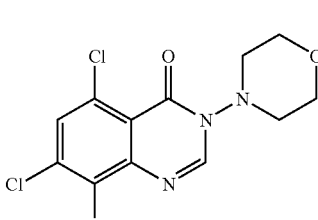 | Neuronal cells: 105, 70 M17 cells: 95.9, 80.9 | 316.1 | 1.84 | 10 days, none | Up to 45.2 ng/mL | |

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 5-Cl, 7-Cl, 8-OH quinazolinone with 4-methylpiperazin-1-yl | Neuronal cells: 96, 91 | 329.2 | 2.41 | 10 days, none | Up to 207 ng/mL | |
| 5-Cl, 7-Cl, 8-OH quinazolinone with 5-methylthiazol-2-yl | Neuronal cells: 94, 70 | 328.2 | 2.10 | 10 days, mild signs | | |
| 5-Cl, 7-Cl, 8-OH quinazolinone with 1-methylbenzimidazol-2-yl | Neuronal cells: 105, 97 M17 cells: 106.9, 94.9 | 361.2 | 2.67 | 10 days, none | Up to 112.4 ng/mL | |
| 5-Cl, 7-Cl, 8-OH quinazolinone with (2-methylthiazol-4-yl)methyl | Neuronal cells: 100, 93 M17 cells 97, 95.7 | 342.2 94.03 | 2.37 | 10 days, none | Up to 2439 ng/mL | 0.10 at 5 min, 0.10 at 60 min |
| 5-Cl, 7-Cl, 8-OH quinazolinone with (3,5-dimethylisoxazol-4-yl)methyl | Neuronal cells: 99, 72 M17 cells 104.3, 76 | 340.2 78.9 | 1.95 | 10 days, none | Up to 3644 ng/mL | 0.18 at 5 min, 0.08 at 60 min |
| 5-Cl, 7-Cl, 8-OH quinazolinone with piperidin-1-yl | Neuronal cells: 98, 51 M17 cells 87.9, 72.7 | 314.2 | 2.94 | 10 days, none | | |

-continued

|  | In vivo Efficacy and Safety Profile | | | | |
|---|---|---|---|---|---|
|  | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 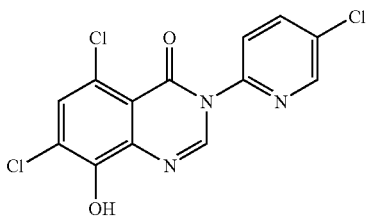 | Neuronal cells: 94, 58 M17 cells 86.9, 70.5 | 342.6 | 2.53 | 10 days, none | | |
| 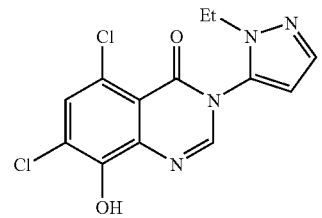 | Neuronal cells: 102, 94 | 325.2 | 1.94 | 10 days, none | Up to 3896 ng/mL | |
| 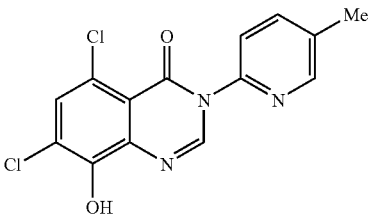 | Neuronal cells: 96, 83 | 322.2 | 2.31 | 10 days, none | Up to 39 ng/mL | |
| 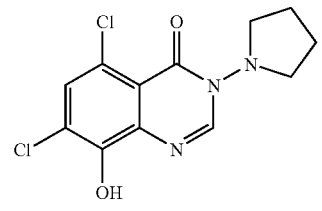 | Neuronal cells: 101, 88 | 300.1 | 2.38 | 10 days, none | | |
| 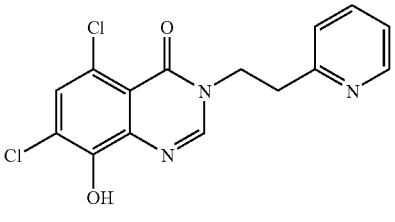 | Neuronal cells: 100, 92 | 336.2 | 2.36 | 10 days, none | Up to 59 ng/mL | |
| 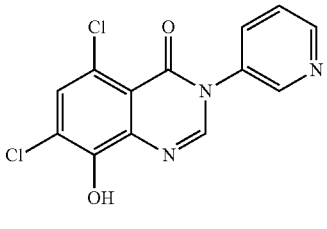 | Neuronal cells: 95, 81 M17 cells: 100.9, 80.5 | 308.1 | 1.81 | 10 days, none | Up to 142.9 ng/mL (single dose) | |

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 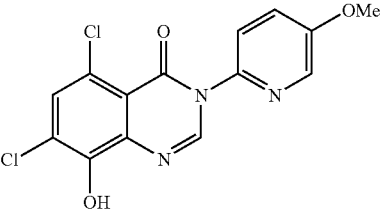 | Neuronal cells: 122, 93 | 338.2 | 2.58 | 10 days, none | Up to 80 ng/mL (single dose) | |
| 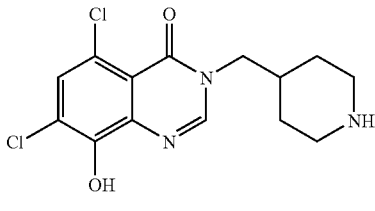 | Neuronal cells: 97, 96 | 328.2 | 1.99 | | | |
| 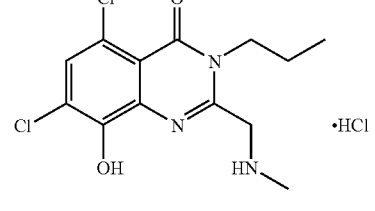 | Neuronal cells: 110, 102 | 316.2 | 2.19 | | | |
| 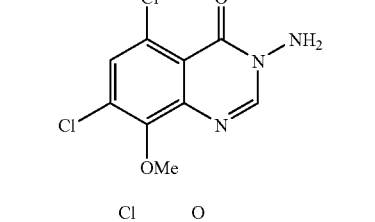 | Neuronal cells: 99, 93 | | | | | |
| 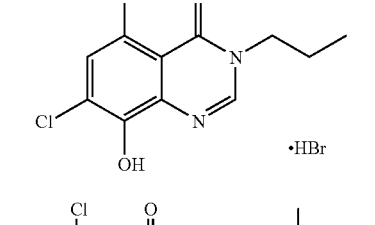 | Neuronal cells: 102, 83 M17 cells 106.7, 98.8 | 273.12 | 2.82 | 10 days, none | Up to 2641 ng/mL | |
| 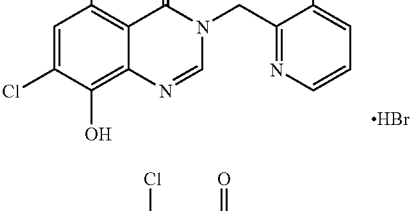 | Neuronal cells: 99, 88 | 336.2 | 2.48 | 10 days, 3/4 mild signs | Up to 439 ng/mL | |
| 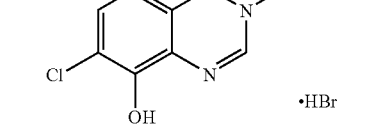 | Neuronal cells: 103, 101 M17 cells 112.7, 103.6 | 246.0 | 2.50 | | | |

-continued

| | In vivo Efficacy and Safety Profile | | | | |
|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |

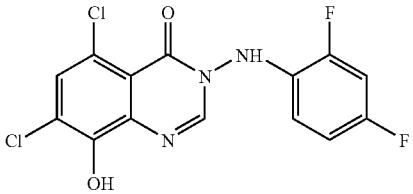

Neuronal cells: 100, 92
M17 cells 105.1, 83.1 | 358.1 | 3.13 | 10 days, none | Up to 1,130.6 ng/mL |

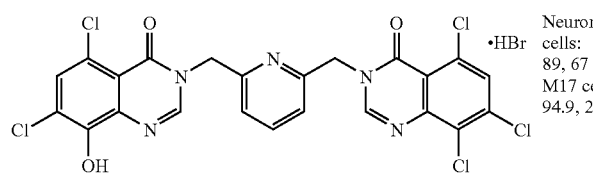

Neuronal cells: 89, 67
M17 cells 94.9, 26.8 | 565.2 | 3.42 | 10 days, none |

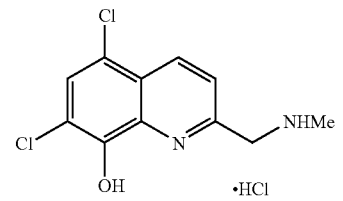

Neuronal cells: 86, 78 | 293.58 | 2.71 |

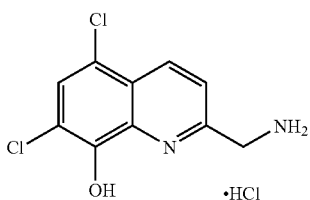

Neuronal cells: 100, 80 | 279.55 | 2.29 |

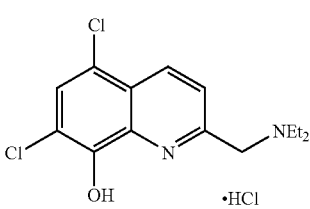

Neuronal cells: 74, 70 | 335.66 | 4.23 |

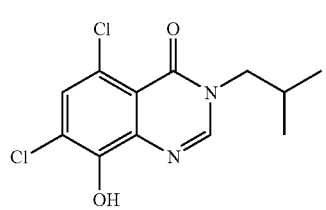

Neuronal cells: 99, 70
M17 cells 101.8, 75.6 | 287.1 | 3.22 | 10 days, none | Up to 1802 ng/mL |

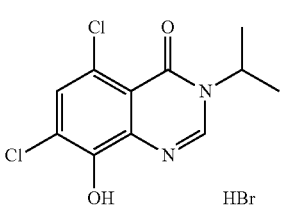

Neuronal cells: 104, 71
M17 cells 94.3, 74.5 | 273.1 | 2.60 | 10 days, none | Up to 383 ng/mL |

-continued
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| 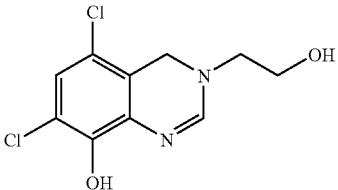 | Neuronal cells: 107, 96 M17 cells 115.3, 118.7 | 275.1 | 1.23 | 10 days, none | Up to 8134.8 ng/mL | |
| 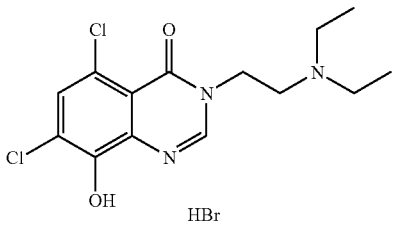 | Neuronal cells: 107, 77 M17 cells: 100.5, 70.3 | 330.2 | 3.24 | 10 days, none | Up to 113.2 ng/mL (single dose) | |
| 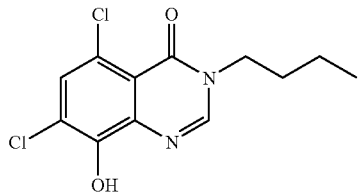 | Neuronal cells: 104, 85 M17 cells 105.4, 95.4 | 287.1 | 3.35 | | | |
| 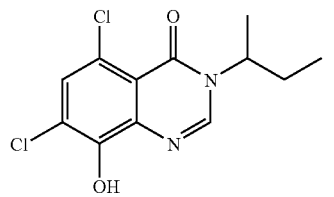 | Neuronal cells: 94, 67 M17 cells 99.2, 68.6 | 287.1 | 3.13 | 10 days, none | Up to 2949 ng/mL | |
| 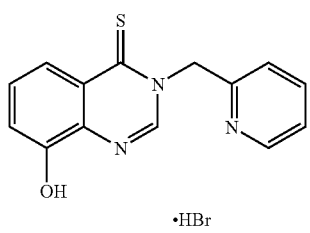 | Neuronal cells: 97, 90 | 269.3 | 1.76 | | | |
| 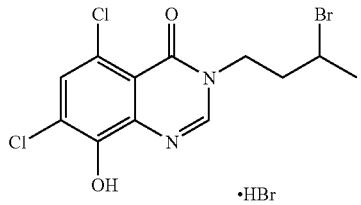 | Neuronal cells: 101, 73 | 366.0 | 3.35 | | | |
| 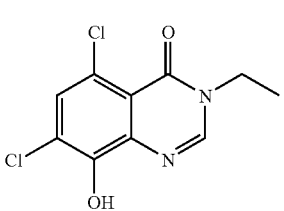 | Neuronal cells: 93, 58 M17 cells 104.3, 95.9 | 259.1 | 2.29 | | | |

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 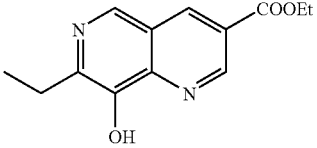 | Neuronal cells: 103, 92 | 246.3 | 3.02 | | | |
| 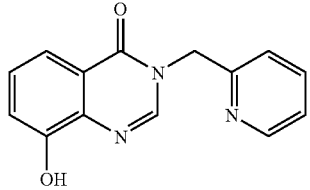 | M17 cells 109.2, 96 | 253.3 | 0.87 | | | |
| 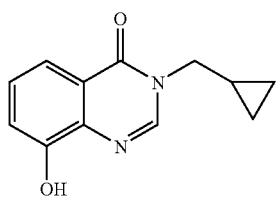 | M17 cells 103.9, 110.8 | 216.2 | 1.58 | | | |
| 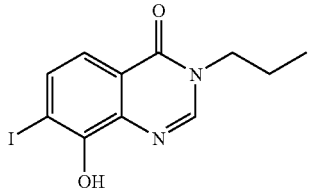 | | 330.1 | 2.48 | 10 days, none | Up to 1096 ng/mL (single dose) | |
| 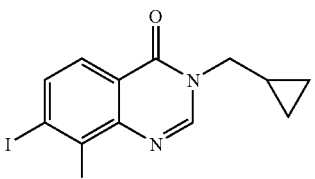 | M17 cells 110.9, 65.1 | 342.1 52.9 | 2.40 | 10 days, none | Up to 2508 ng/mL | 0.07 at 5 min, 0.06 at 60 min |
| 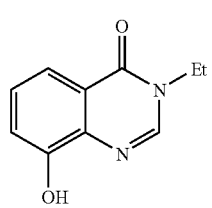 | | 190.2 | 1.13 | | | |
| 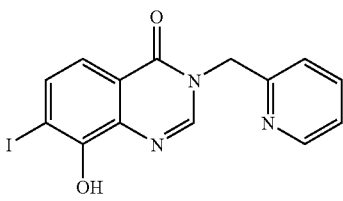 | M17 cells: 93.8, 84.5 | 379.2 | 1.69 | 10 days, none | Up to 1538 ng/mL | |

-continued
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| 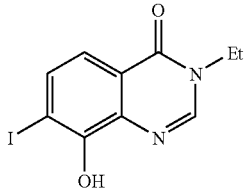 | | 316.1 | 1.95 | 10 days, none | | |
| 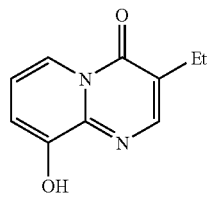 | M17 cells 96.1, 27.1 | 190.2 | 0.84 | | | |
| 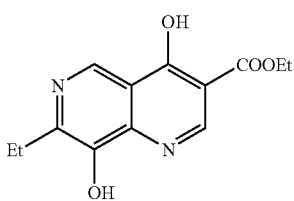 | | 262.3 | 3.92 | | | |
| 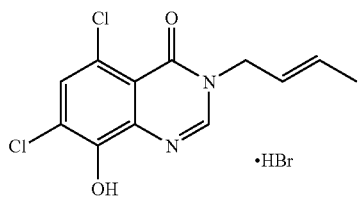 | | 285.1 | 3.07 | | | |
| 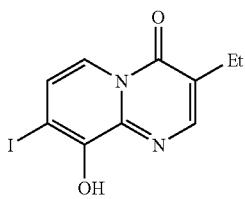 | M17 cells 82.5, 23.3 | 316.1 | 1.63 | At 10 mg/kg 10 days, none | At 10 mg/kg: Up to 7082 ng/mL | |
| 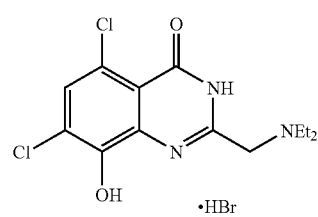 | M17 cells 106.5, 99.1 | 316.2 | 2.55 | 10 days, none | Up to 2289 ng/mL | |
| 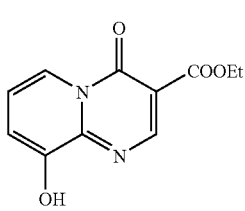 | | 234.2 | 0.35 | | | |

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 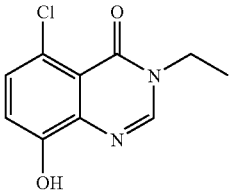 | M17 cells 100.6, 85.4 | 224.6 | 1.89 | | | |
| 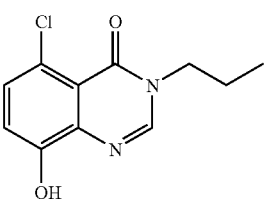 | M17 cells 89.4, 79.4 | 238.7 | 2.42 | | | |
| 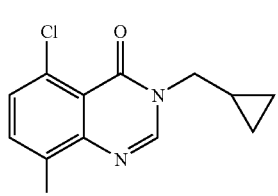 | M17 cells: 86.3, 57.6 | 250.7 | 2.34 | | | |
| 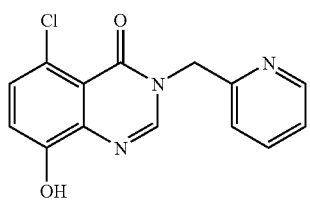 | M17 cells 93.6, 88.4 | 287.7 | 1.63 | | | |
| 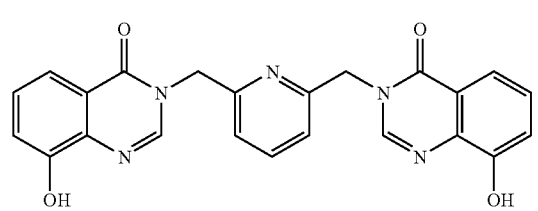 | M17 cells: 117.1, 105.6 | 427.4 | 1.10 | 10 days, none | Up to 128.4 ng/mL | |
| 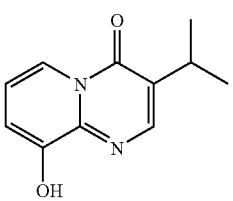 | M17 cells 99.7, 45.6 | 204.2 | 1.24 | 10 days, none | Up to 409 ng/ml | |
| 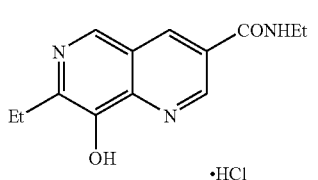 | M17 cells: 84.4, 92.1 | 245.3 | 2.56 | | Up to 125.5 ng/mL (Single dose) | |

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 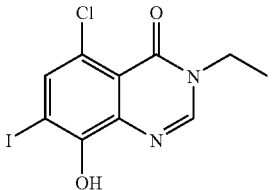 | M17 cells: 100.8, 50.4 | 350.5 | 2.68 | 10 days, 2/4 deaths | Up to 1802 ng/mL | |
| 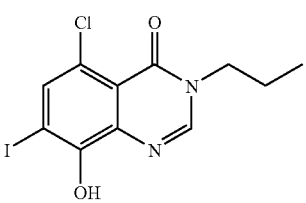 | M17 cells: 120.2, 100.2 | 364.6 | 3.21 | | Up to 4060 ng/mL | |
| 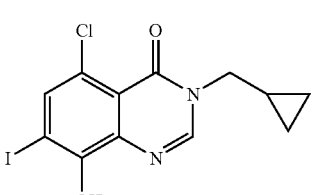 | M17 cells: 97.9, 82.3 | 376.6 | 3.13 | At 10 mg/kg: 10 days, none | | |
| 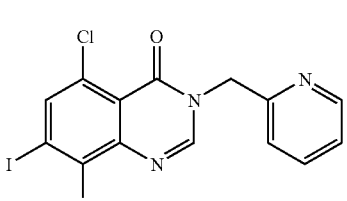 | M17 cells: 102.2, 99.2 | 413.6 | 2.42 | | | |
| 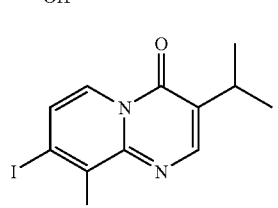 | M17 cells: 96.7, 44.2 | 330.12 | 2.03 | 10 days, 1/4 death, remaining 1/3 mild sings | | |
| 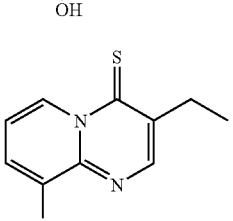 | M17 cells: 93.3, 73.7 | 206.27 | 1.66 | | | |
| 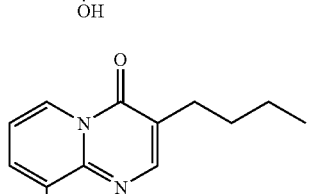 | M17 cells: 73.6, 37 | 218.25 | 1.90 | 10 days, none | | |

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| (structure: 3-butyl-7-iodo-9-hydroxy-4H-pyrido[1,2-a]pyrimidin-4-one) | M17 cells: 101.7, 58.7 | 344.15 | 2.69 | 10 days, 2/4 deaths | | |
| (structure: 5,7-dichloro-2-((dimethylamino)methyl)-8-hydroxyquinazolin-4(3H)-one ·HBr) | M17 cells 97.4, 100.3 | 288.13 | 1.50 | 10 days, none | Up to 642.6 ng/mL | |
| (structure: 3-butyl-9-hydroxy-4H-pyrido[1,2-a]pyrimidine-4-thione) | | 234.32 | 2.72 | 7 days, 2/4 deaths | Up to 57 ng/ml | |
| (structure: 9-hydroxy-3-propyl-4H-pyrido[1,2-a]pyrimidin-4-one) | M17 cells 79.1, 45.2 | 204.23 | 1.37 | 10 days, none | Up to 690 ng/ml | |
| (structure: 9-hydroxy-7-iodo-3-propyl-4H-pyrido[1,2-a]pyrimidin-4-one) | M17 cells 80.8, 47.6 | 330.12 52.9 | 2.16 | 10 days, none | Up to 11742 ng/ml | 0.02 at 5 min, 0.03 at 60 min |
| (structure: 8-hydroxy-7-iodo-3-isobutylquinazolin-4(3H)-one) | M17 cells: 111.2, 68.2 | 344.15 | 2.88 | At 10 mg/kg: 10 days, none | At 10 mg/kg: Up to 309 ng/ml | |
| (structure: 8-hydroxy-7-iodo-3-isopropylquinazolin-4(3H)-one) | | 330.12 | 2.26 | 10 days, 1/4 deaths | Up to 277 ng/ml | |

-continued
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| 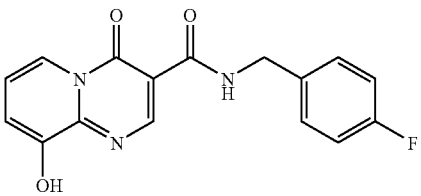 | M17 cells: 76.7, 54.2 | 313.28 | 1.31 | | | |
| 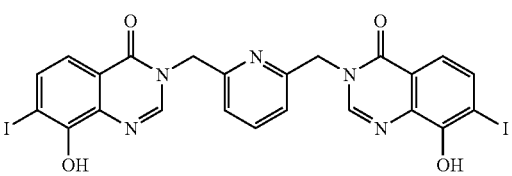 | | 679.21 | 2.74 | | | |
| 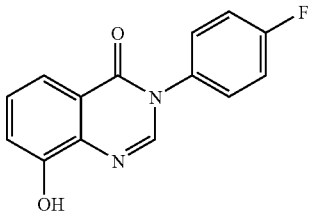 | M17 cells 92.7, 67.5 | 256.23 | 2.19 | | | |
| 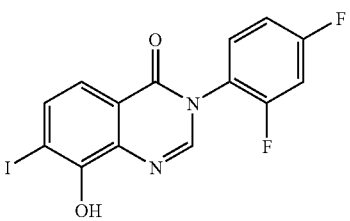 | M17 cells: 90.3, 80.3 | 400.12 | 3.15 | 6 days, 2/4 deaths | | |
| 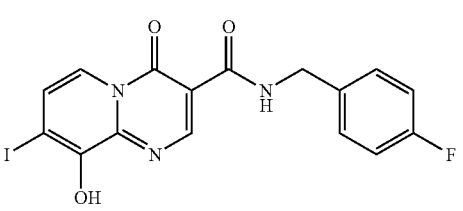 | M17 cells: 89.6, 23.4 | 439.18 | 2.09 | 7 days, 4/4 deaths | | |
| 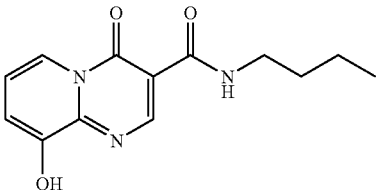 | M17 cells 98.8, 48.4 | 261.28 | 0.78 | | | |
| 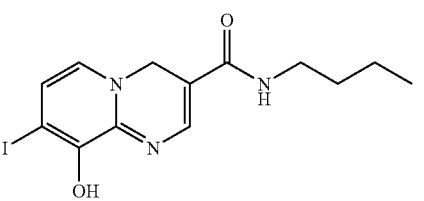 | M17 cells 85.3, 63.4 | 387.17 | 1.56 | 10 days, none | Up to 27,598 ng/ml | |

-continued

| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| | \<In vivo Efficacy and Safety Profile\> | | | | | |

| Structure | Cytotoxicity | Parent MW/PSA | ClogP/ElogD | Toxicity | Mice plasma conc. | B:P |
|---|---|---|---|---|---|---|
| 5,7-dichloro-8-hydroxy-3-methyl-2-(methylaminomethyl)quinazolin-4(3H)-one · HBr | M17 cells 96, 90.6 | 288.13 | 1.13 | 10 days, none | Up to 510.4 ng/mL | |
| 3-(4-fluorophenyl)-7-iodo-8-hydroxyquinazolin-4(3H)-one | M17 cells: 94.6, 30.2 | 382.13 | 2.99 | | | |
| 3-(2-diethylaminoethyl)-7-iodo-8-hydroxyquinazolin-4(3H)-one | M17 cells: 106.5, 41.4 | 387.22 | 2.90 | | | |
| 5-chloro-7-iodo-8-hydroxy-3-(pyridin-3-yl)quinazolin-4(3H)-one | M17 cells: 97.4, 95 | 399.57 | 2.20 | | | |
| 7-iodo-8-hydroxy-3-propylquinazoline-4(3H)-thione | M17 cells 89.9, 86.2 | 346.19 | 3.65 | 10 days, none | Up to 1593 ng/ml | |
| 2-(7-iodo-8-hydroxy-4-oxoquinazolin-3(4H)-yl)-N-propylacetamide | M17 cells: 84.3, 95.5 | 387.17 | 1.81 | | | |
| 2-(7-iodo-8-hydroxy-4-oxoquinazolin-3(4H)-yl)-N,N-diethylacetamide | M17 cells: 92.2, 98.7 | 401.2 | 2.24 | | | |

-continued

| | In vivo Efficacy and Safety Profile | | | | |
|---|---|---|---|---|---|
| Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| M17 cells 85.7, 43 | 332.2 | 3.12 | 10 days, none, 1/4 mild signs | Up to 400 ng/ml | |
| | 442.0 | 3.09 | | | |
| M17 cells: 127.4, 104.8 | 461.2 | 2.76 | | | |
| M17 cells: 60.1, 34.2 | 356.34 | 1.45 | | | |
| | 166.20 | 1.93 | | | |
| M17 cells: 86.3, 38.5 | 358.18 | 3.53 | | | |

-continued
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| 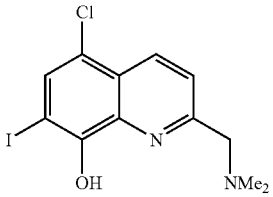 | M17 cells: 97.9, 24.4 | 362.60 | 3.56 | 1 day, 3/4 deaths | | |
| 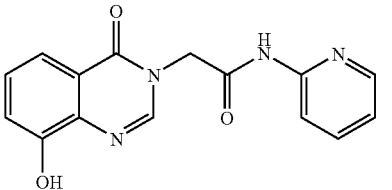 | M17 cells 110.1, 98.2 | 269.28 | 1.12 | | | |
| 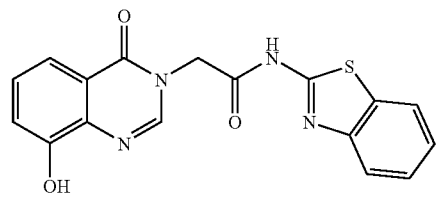 | | 352.37 | 2.62 | | | |
| 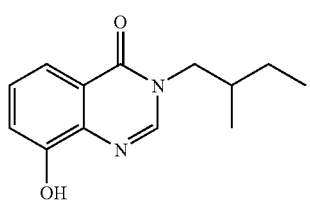 | M17 cells 102.7, 47.2 | 232.28 | 2.59 | | | |
| 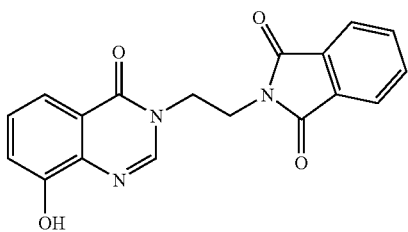 | M17 cells 103.9, 106.5 | 335.31 | 1.94 | | | |
| 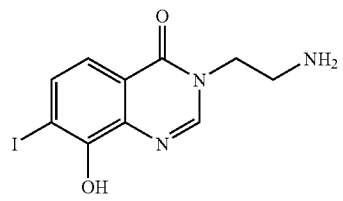 | | 331.11 | 0.97 | | | |
| 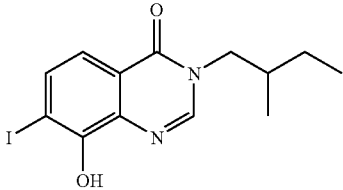 | M17 cells: 42.8, 19.3 | 358.18 | 3.41 | | | |

-continued
| | | | In vivo Efficacy and Safety Profile | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 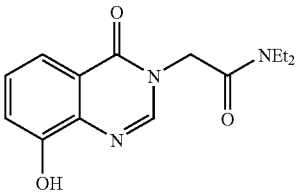 | M17 cells 118.3, 102.1 | 275.30 | 1.42 | | | |
| 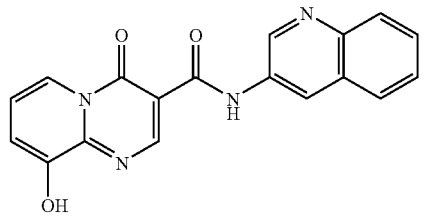 | M17 cells 102.1, 32.84 | 332.31 | 1.27 | | | |
| 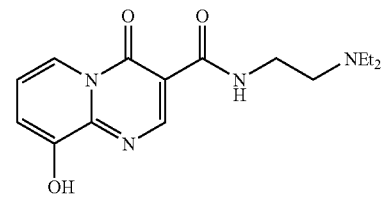 | M17 cells 115.2, 102.7 | 304.34 | 0.66 | | | |
| 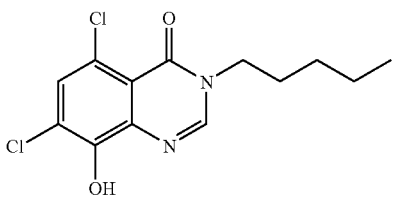 | M17 cells 81.3, 56.8 | 301.17 | 3.88 | | | |
| 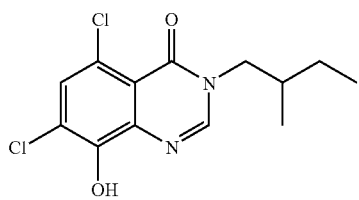 | M17 cells 85.1, 39.4 | 301.17 | 3.75 | | | |
| 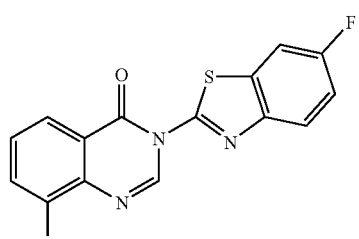 | M17 cells 99.1, 73.7 | 313.31 | 2.21 | | | |

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 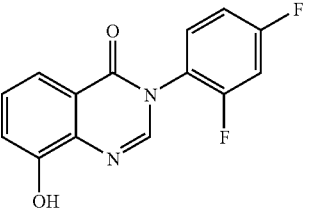 | M17 cells 104.5, 103.7 | 274.22 | 2.34 | | | |
| 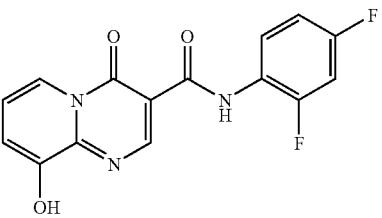 | M17 cells 99.4, 67.1 | 317.25 | 0.68 | | | |
| 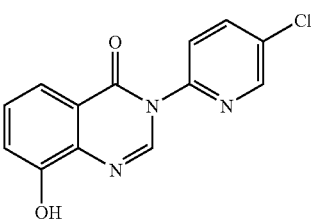 | M17 cells: 106.9, 122.1 | 273.67 | 1.40 | 10 days, none | Up to 6 ng/mL | |
| 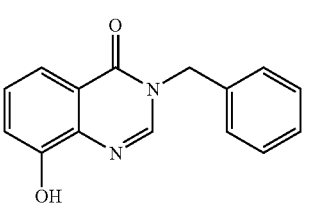 | M17 cells: 98.5, 90.4 | 252.27 | 2.37 | | | Not novel |
| 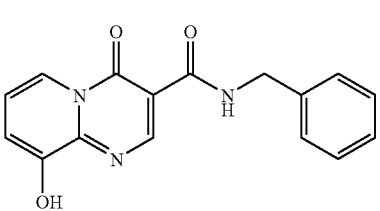 | M17 cells: 92.7, 97.3 | 295.29 | 1.16 | 10 days, none | Up to 22.2 ng/mL | |
| 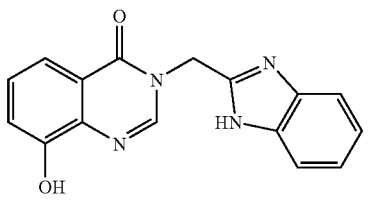 | M17 cells 107, 108.5 | 292.29 | 1.79 | | | |
| 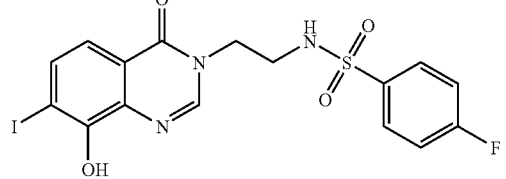 | M17 cells: 96.5, 43 | 489.26 | 3.05 | | | |

-continued
| | | In vivo Efficacy and Safety Profile | | | | |
|---|---|---|---|---|---|---|
| | | | ClogP | | | |
| | Cytotoxicity (% viable at 1 and 10 uM)[a] | Parent MW/ PSA | ElogD (E) or ClogD (C) | Toxicity[b] at 30 mg/kg | Mice plasma concentration[c] | B:P Ratio[d] |
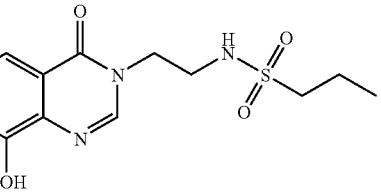
M17 cells: 103.7, 98.6, | 437.25 | 2.04
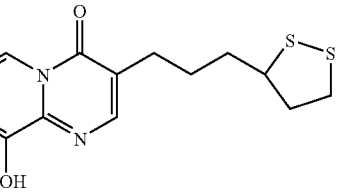
M17 cells 106.1, 27.24 | 308.42 | 2.36
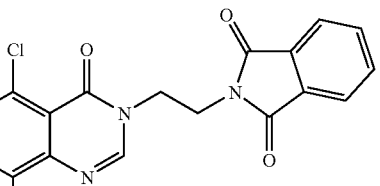
M17 cells 103.8, 101.1 | 404.20 | 3.10
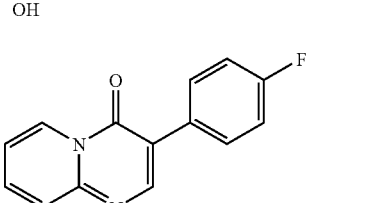
M17 cells 75.3, 33.8 | 256.23 | 2.05
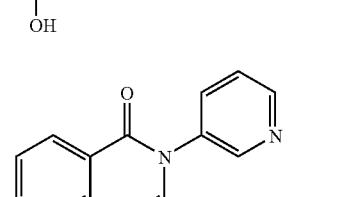
M17 cells 105.5, 109.7 | 239.23 | 0.68
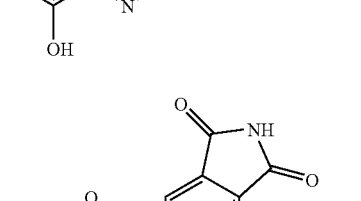
M17 cells 102.5, 102.6 | 307.26 | 1.15

-continued
| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 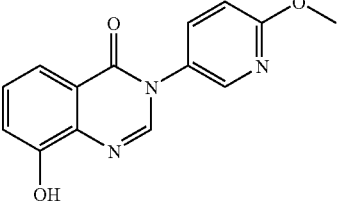 | M17 cells 97.8, 109.7 | 269.26 | 1.45 | | | |
| 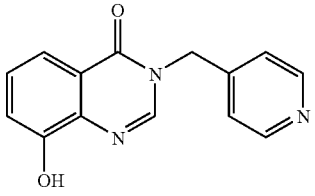 | M17 cells 104.7, 103.5 | 253.26 | 0.87 | | | |
| 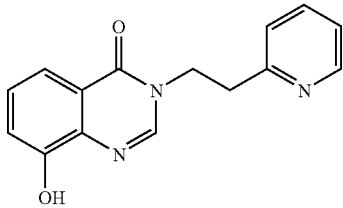 | M17 cells 107, 96.2 | 267.29 | 1.20 | | | |
| 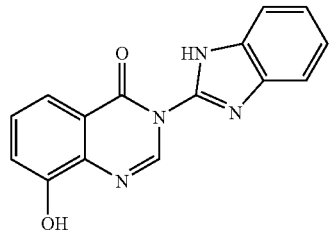 | M17 cells 108.2, 103.4 | 278.27 | 1.62 | | | |
| 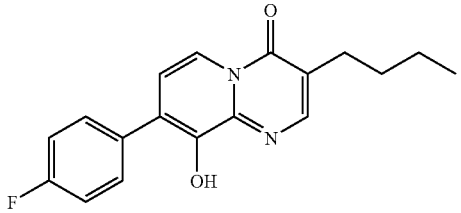 | M17 cells 100.9, 37.9 | 312.34 | 3.43 | | | |
| 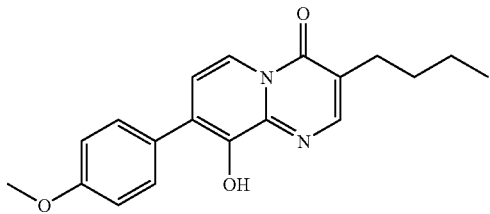 | M17 cells 79.2, 64.4 | 324.37 | 3.21 | | | |

| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| 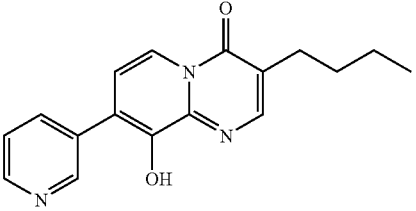 | M17 cells 92.1, 38.2 | 295.34 | 1.80 | | | |
| 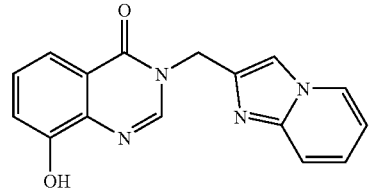 | M17 cells 95, 98.4 | 292.29 | 1.44 | | | |
| 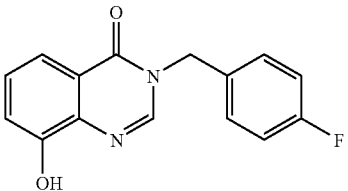 | M17 cells 97.2, 60.5 | 270.26 | 2.51 | | | |
|  | M17 cells 94.5, 59.1 | | | | | |
| 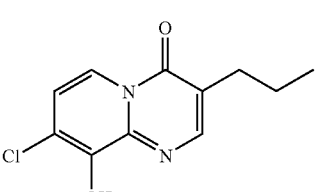 | M17 cells 98.1, 38.9 | | | | | |
| 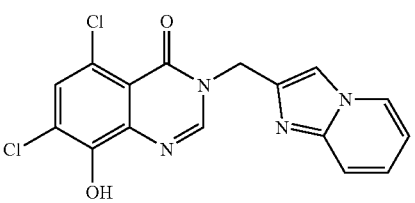 | M17 cells: 109.2, 98.2 | 361.18 | 2.60 | 10 days, none | Up to 98.3 ng/mL | |
| 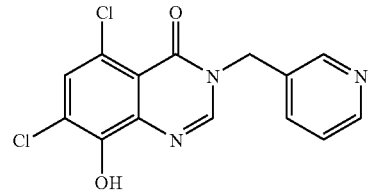 | M17 cells 105.7, 95.4 | 322.15 | 2.03 | 10 days, none | Up to 4023.4 ng/mL | |

-continued

| | In vivo Efficacy and Safety Profile | | | | | |
|---|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| [Structure: 5,7-dichloro-8-hydroxy-3-(pyridin-4-ylmethyl)quinazolin-4(3H)-one] | M17 cells 105.4, 90.4 | 322.15 | 2.03 | 10 days, none | Up to 2181.1 ng/mL | |
| [Structure: 5,7-dichloro-8-hydroxy-3-(pyridin-2-yl)quinazolin-4(3H)-one] | M17 cells: 107.8, 89.2 | 308.12 | 1.81 | 10 days, none | Up to 144.2 ng/mL | |
| [Structure: 5,7-dichloro-8-hydroxy-3-((1-methyl-1H-imidazol-2-yl)methyl)quinazolin-4(3H)-one] | M17 cells 107.5, 97.6 | 325.15 | 1.34 | 10 days, none | Up to 13214.8 ng/mL | |
| [Structure: 5,7-dichloro-8-hydroxy-3-(1H-pyrazol-3-yl)quinazolin-4(3H)-one] | M17 cells 125.7, 114.8 | 297.10 | 1.69 | 10 days, none | Up to 1477.4 ng/mL | |
| [Structure: 3-(benzo[d]thiazol-2-yl)-5,7-dichloro-8-hydroxyquinazolin-4(3H)-one] | M17 cells 82.7, 63.9 | 364.21 | 3.197 | | | |
| [Structure: 5,7-dichloro-8-hydroxy-3-(1H-indazol-5-yl)quinazolin-4(3H)-one] | M17 cells: 96.2, 88.9 | 347.16 | 2.78 | 10 days, none | Up to 126 ng/mL | |

-continued

| | In vivo Efficacy and Safety Profile | | | | |
|---|---|---|---|---|---|
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| | M17 cells 85.4, 93.3 | 376.15 | 2.297 | 10 days, none | | |
| | M17 cells 93, 98 | 414.26 | 1.79 | | | |
| | M17 cells 105, 100.7 | 289.08 | 1.63 | 10 days, none | | |
| | M17 cells 95.1, 93.9 | 337.17 | 1.71 | 10 days, 1 of 4 deaths | | |
| | M17 cells 102.8, 62.1 | 376.25 | 3.24 | | | |
| | M17 cells 105.4, 105.1 | 361.18 | 2.60 | 10 days, none | Up to 1465.4 ng/mL | |

-continued

|  | In vivo Efficacy and Safety Profile | | | | | |
|---|---|---|---|---|---|---|
|  | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
| 5,7-dichloro-8-hydroxy-3-((1-methylpyrrolidin-2-yl)methyl)quinazolin-4(3H)-one·HBr | M17 cells 106.6, 93.9 | 328.20 | 2.57 | 10 days, none | Up to 382.5 ng/mL |  |
| 5,7-dichloro-8-hydroxy-3-(thiazol-2-ylmethyl)quinazolin-4(3H)-one | M17 cells 96, 99.8 | 328.17 | 1.88 | 10 days, none | Up to 441.4 ng/mL |  |
| 4-(5,7-dichloro-8-hydroxy-4-oxoquinazolin-3(4H)-yl)butanoic acid | M17 cells 109.7, 102.9 | 317.12 | 1.92 | 10 days, none | Up to 17008 ng/mL |  |
| 3-((1H-benzo[d]imidazol-2-yl)methyl)-5,7-dichloro-8-hydroxyquinazolin-4(3H)-one | M17 cells 101.5, 100.4 | 361.18 | 2.95 | 10 days, none | Up to 2796 ng/mL |  |
| 3-(benzo[d]thiazol-2-ylmethyl)-5,7-dichloro-8-hydroxyquinazolin-4(3H)-one | M17 cells 111.1, 80.9 | 378.23 | 3.47 | 10 days, none | Up to 166.1 ng/mL |  |
| 6,8-dichloro-9-hydroxy-2,3-dihydropyrrolo[2,1-b]quinazolin-1(4H)-one | M17 cells 115.1, 93.9 | 271.1 | 2.28 |  |  |  |
| 3-((1-benzylpiperidin-4-yl)methyl)-5,7-dichloro-8-hydroxyquinazolin-4(3H)-one·HBr | M17 cells 109.1, 83.4 | 418.23 | 4.23 |  |  |  |

-continued
| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| 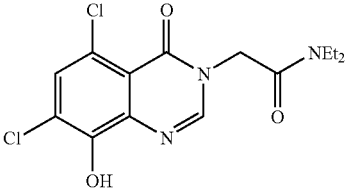 | M17 cells 122.3, 104.1 | 344.19 | 2.58 | | | |
| 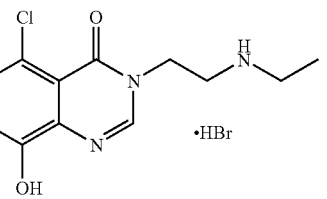 | M17 cells 100, 106.9 | 302.16 64.9 | 2.12 | | | |
| 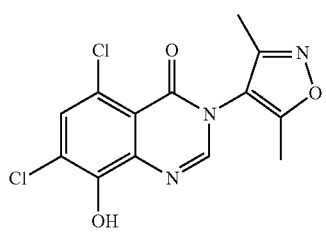 | M17 cells 106.5, 94.2 | 326.14 | 1.84 | 10 days, none | Up to 7107 ng/mL | |
| 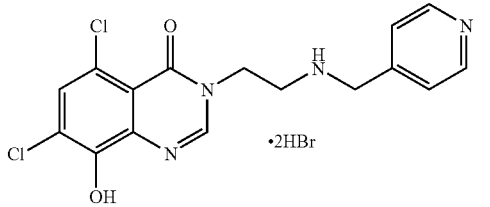 | M17 cells 103, 104.8 | 365.21 | 2.02 | 10 days, none | Up to 1639.8 ng/mL | |
| 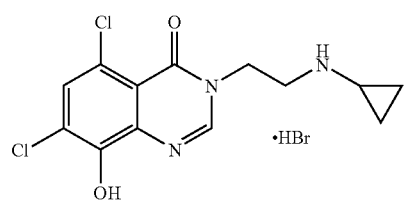 | M17 cells 98.8, 96.2 | 314.17 | 1.95 | | | |
| 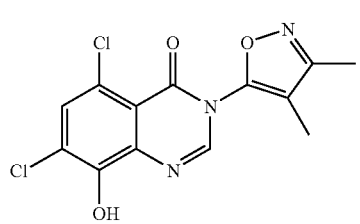 | M17 cells 99.6, 95.4 | 326.13 | 1.79 | | | |
| 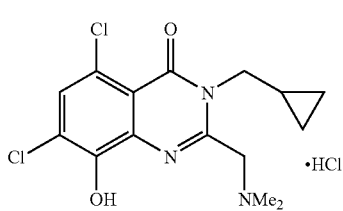 | M17 cells 94.4, 74.5 | 342.22 | 2.57 | 10 days, none | Up to 1166.6 ng/mL | |

| | Cytotoxicity (% viable at 1 and 10 uM)[a] | Parent MW/ PSA | ClogP ElogD (E) or ClogD (C) | Toxicity[b] at 30 mg/kg | Mice plasma concentration[c] | B:P Ratio[d] |
|---|---|---|---|---|---|---|
| 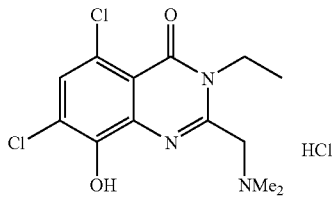 | M17 cells 99.2, 102.1 | 316.18 | 2.13 | 10 days, none | Up to 975.9 ng/mL | |
| 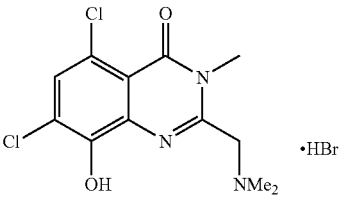 | M17 cells 104, 110.7 | 302.156 | 1.60 | 10 days, 1 of 4 mild signs | Up to 492.1 ng/mL | |
| 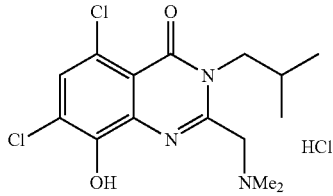 | M17 cells 104.4, 61.5 | 344.34 | | | | |
| 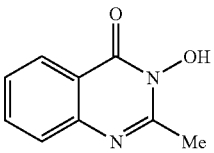 | M17 cells 100.6, 114.7 | 176.18 | | | | |

[a] Viability of primary cortical neuronal cultured cells (Neuronal cells) or M17 human neuroblastoma cells (M17 cells) in the presence of test compound at concentrations of 1 and 10 μM.
[b] Visual observations
[c] Confirmation of presence of compound in plasma at one or two time points (between 30 min and 4 h) Brain uptake of test compound following IV administration to male Swiss Outbred mice at a nominal dose of 5 mg/kg. Results are expressed as the brain: plasma ratio at 5 min and 60 min post dose.

Example 3

Testing Compounds for In Vitro and In Vivo Efficacy

Twelve compounds were screened for in vitro efficacy and 4 were tested for in vivo efficacy.

Emulsion carrier was used as a control for the in vitro and in vivo test systems. All the compounds were tested initially via in vitro testing to determine an efficacy profile with three glioma cell lines and a control cell line. The results are shown in FIGS. 2 to 5.

Experimental Design
In Vitro Efficacy Protocol

The in vitro efficacy of the test articles were analyzed via the MTT cell viability assay.

Figure 4:
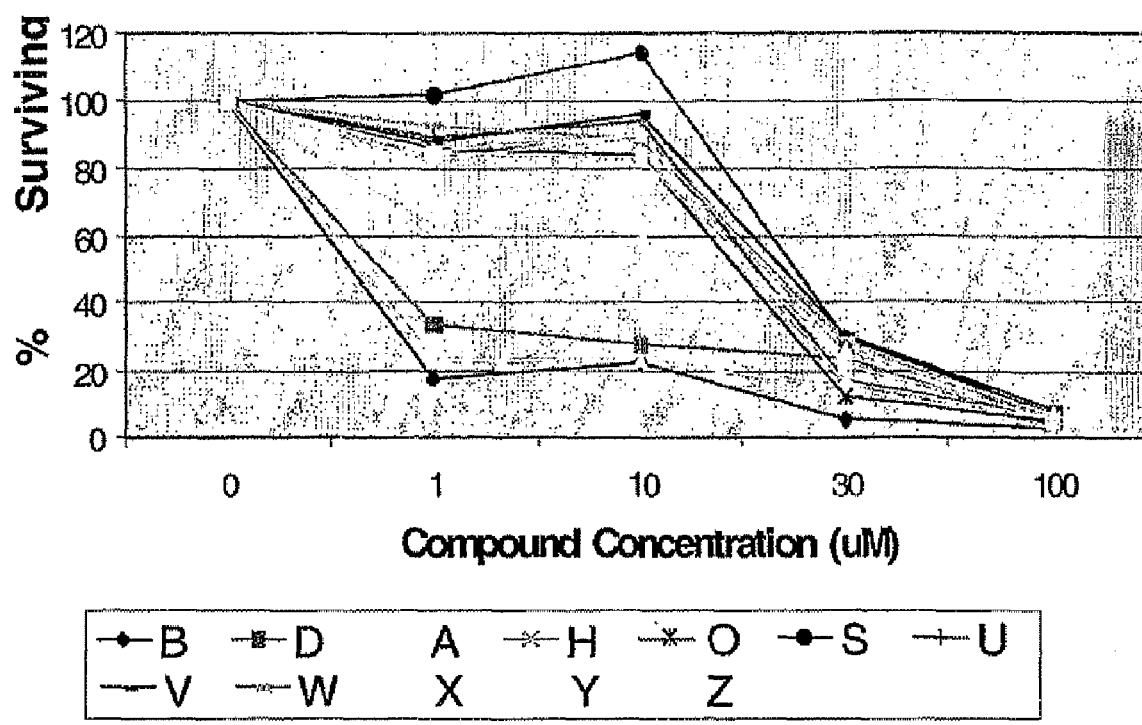
FIG. 4 is a graph showing a cytotoxicity screen of compounds on SMA 560 cells. The compounds tested are designated by letter and are defined in the specification.
Figure 5:
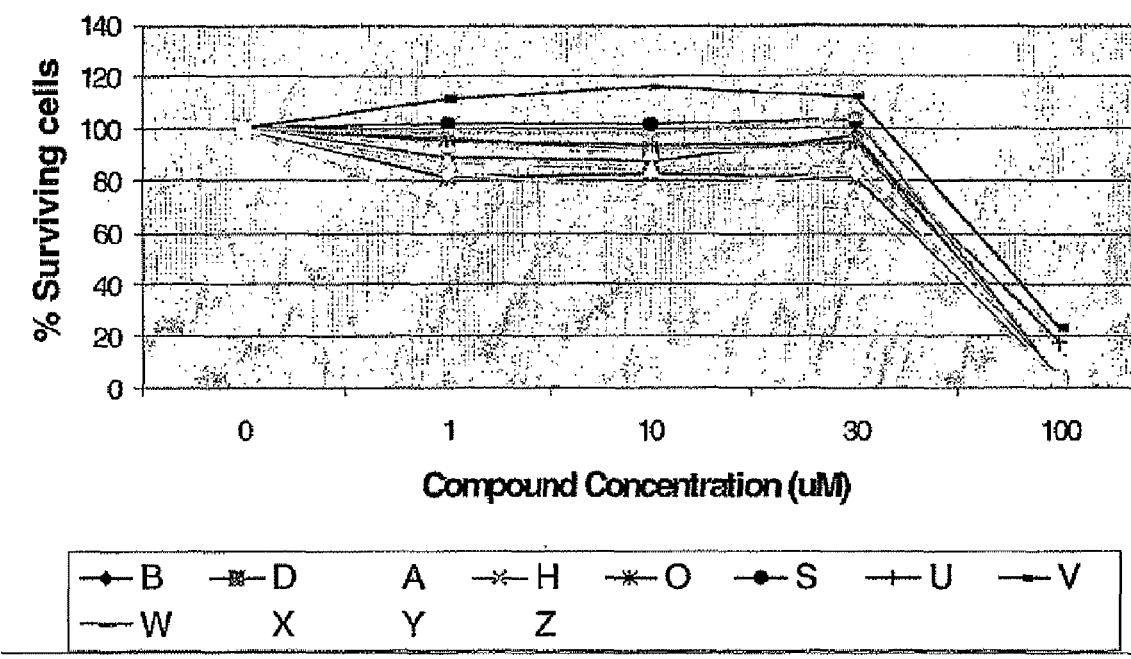
FIG. 5 is a graph showing a cytotoxicity screen of compounds on 3T3 cells. The compounds tested are designated by letter and are defined in the specification.

The following cell lines were used to determine cell viability on exposure to the test articles: C6—rat glioma cell line (FIG. 1), VMDK—mouse glioma cell line (FIG. 3), U87MG—human glioma cell line (FIG. 2), 3T3—Control cell line (FIG. 4).

Cells were plated in 96 well plates with 100 μl of cell culture medium and be allowed to adhere over 24 hours allowing for approximately 50% confluence. At 24 hours, the cell medium was replaced with fresh cell culture medium containing compounds or the carrier emulsions.

The cells will then be incubated and grown for a designated period (72 hours) after which the MTT solution were added to the wells and incubated at 37° C. for 1-2 hours. The absorbance of each well will then be measured with a plate reader at 570 nm. The efficacy profiles were calculated relevant to the cells incubated in the absence of the compounds over the course of the experiment.

In Vivo Efficacy Protocol 2 doses were used: at the maximum tolerated dose and one level below the maximum tolerated dose.

3 mouse models are employed:
  C6—xenograft mouse model (glioma model)
  SMA560—VMDK Mouse Model (glioma model)
  U87MG—nude mouse model
C6—CBA Xenograft Model (ATCC Number: CCL-107)
  This model is used to screen 4 compounds.
SMA560—VMDK Mouse Model (ATCC Number: CCL-163)
  This model is used to screen the 4 compounds screened previously with the C6 xenograft model.
U87MG Nude Mouse Model (ATCC Number: CRL-9589)

This model is used to screen 2 compounds.

Initially, CBA mice are used to receive an intracranial inoculation of the C6 glioma cells. Briefly, $1 \times 10^6$ cells are inoculated into the left hemisphere via at day 5 post C6 cell inoculation. The mice receive daily intraperitoneal (ip) administration of test articles in a carrier emulsion or carrier emulsion alone as a control for 8 days until day 12. At day 14, the mice are euthanised via $CO_2$ inhalation and the brain removed for histological processing.

The VMDK mouse strain is then used to screen the identical test articles and carrier emulsions as per the C6 xenograft model in the CBA mice. The VMDK mice received an inoculation of $1 \times 10^5$ SMA560 cells into the left hemisphere via standard methods. At day 5 post SMA560 cell inoculation, the mice receive daily ip administration of agents in a carrier emulsion or carrier emulsion alone as a control for 12 days until day 16. Identical doses of test articles and carrier emulsions as used in the C6 xenograft model are used with the SMA560 model. At day 18, the mice are euthanized via $CO_2$ inhalation and the brain removed for histological processing.

A nude mouse model utilizing the U87MG human glioma cell line is used to screen agents. The nude mouse Nu/nu strain receives an inoculation of $1 \times 10^6$ U87MG cells into the left hemisphere. At day 5 post U87MG cell inoculation, the mice receive daily ip administration of the agent or carrier emulsion alone as a control for 12 days until day 16. At day 18, the mice are euthanised via $CO_2$ inhalation and the brain removed for histological processing.

Haematoxylin and eosin stained sections are used to measure tumor dimensions in order to determine the efficacy of the test compounds on tumor growth relative to the control mice.

The results of the effects of compounds A, B, S and H are shown in FIGS. 6a to d.

The graphs can be summarized as follows:

Y-axis refers to the tumor area in pixels.

The numbers in the bars refer to the total mice in each group (mice that were found dead very early or brains could not be sampled due to the head being chewed by other mice were not included).

The numbers with the asterix refer to the groups were mice may have been culled 1 or 2 days early due to being ill or found dead. These have been included in the final calculations as their tumors were fairly large and were they were culled close to the final cull point.

Example 4

Clinical Development of Compound B

Compound B was administered to healthy volunteers in a 2-part study comprising single dose administration (Stage A) and multidose administration (Stage B). Overall, Compound B was generally well tolerated as a single dose in young male volunteers and up to 7 days of treatment in elderly healthy volunteers.

The objectives of the Phase I trials were to determine the safety, tolerability and pharmacokinetics of single and multiple oral doses of Compound B in healthy volunteers. The double-blind studies were conducted at a Phase I unit in The Netherlands. The protocol included safety measures designed to capture the potential human adverse effects. A total of 65 healthy subjects have been exposed to doses of Compound B (41 single dose, 24 multiple dose).

| Disposition of Subjects - Stages A & B | | | | | | | | | | | |
|---|---|---|---|---|---|---|---|---|---|---|---|
| | | Number of Subjects (N) | | | | | | | | | |
| | | | Compound B (mg) | | | | | | | | |
| Stage | Sex | Placebo | 25 | 50 | 100 | 200 | 300 | 400 | 500 | 600 | 800 | Total |
| A | M | 14 | 5 | 6 | 6 | 6 | 6 | — | 6 | — | 6 | 55 |
| B | M | 4 | — | — | — | 3 | — | 3 | — | 3 | 3 | 16 |
|   | F | 4 | — | — | — | 3 | — | 3 | — | 3 | 3 | 16 |
| Total | | 8 | — | — | — | 6 | — | 6 | — | 6 | 6 | 32 |

Safety and Tolerability Stage A—Single Dose

In Stage A, fifty five (55) healthy male subjects aged 18-50 years were randomised (3:1) to receive a single oral dose of either placebo or Compound B at one of 7 dose levels (25, 50, 100, 200, 300, 500 or 800 mg).

Analysis from Stage A demonstrated that Compound B, when administered as a single oral dose, was well tolerated in healthy male volunteers aged 18 to 50 years. There was no difference in the incidence of adverse events between the Compound B (43.9%) and placebo arms (42.9%).

Safety and Tolerability Stage B—Multiple Dose

In Stage B, thirty two (32) healthy male and female subjects aged 45-75 years (eight subjects per dose level) were randomised (3:1) to receive a daily oral dose over 7 consecutive days of either placebo or Compound B at one of 4 dose levels (200, 400, 600 or 800 mg). Each dose level comprised of 4 males and 4 females; the randomisation schedule ensuring that 1 subject/sex received placebo and 3 subjects/sex received Compound B.

Analysis of Stage B indicates that Compound B was generally well tolerated in healthy elderly subjects.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Bevan and Lloyd, *Anal. Chem.* 72:1781-1787, 2000
Goodman and Gilman's, *The Pharmacological Basis for Therapeutics* 7th ed., 1985
Lombardo et al, *J. Med. Chem.* 43:2922-2928, 2000
Remington's Pharmaceutical Sciences, 20th ed. Williams and Wilkins, 2000
The British National Formulary 43rd ed., British Medical Association and Royal Pharmaceutical Society of Great Britain, 2002

The invention claimed is:

1. A method for the treatment of a glioma brain tumor in a subject in need thereof comprising administering an effective amount of a compound of formula (IC):

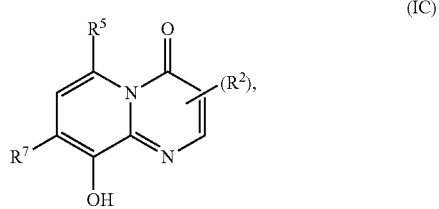

(IC)

in which $R^2$ is H; optionally substituted $C_{1-6}$ alkyl; optionally substituted $C_{2-6}$ alkenyl; optionally substituted $C_{2-6}$ alkynyl; optionally substituted $C_{3-6}$ cycloalkyl; optionally substituted aryl; CN; $OR^6$, $SR^6$, $COR^6$, $CSR^6$, $HCNOR^6$ or $HCNNR^6$ in which $R^6$ is H, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl or optionally substituted heterocyclyl; $NR^8R^9$ or $SO_2NR^8R^9$ in which $R^8$ and $R^9$ are independently selected from H, optionally substituted $C_{1-6}$alkyl, optionally substituted $C_{2-6}$ alkenyl, optionally substituted $C_{2-6}$ alkynyl, optionally substituted $C_{3-6}$ cycloalkyl, optionally substituted aryl and optionally substituted heterocyclyl; $CONR^9R^{10}$ in which $R^9$ is as defined above and $R^{10}$ is optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl or optionally substituted heterocyclyl; $CH_2CONR^8R^9$ in which $R^8$ and $R^9$ are as defined above; and $(CH_2)_nNR^9R^{11}$ in which $R^9$ is as defined above and $R^{11}$ is selected from optionally substituted $C_{1-6}$ alkyl, optionally substituted $C_{2-6}$ alkenyl, optionally substituted alkynyl, optionally substituted $C_{3-6}$ cycloalkyl, optionally substituted aryl, optionally substituted heterocyclyl and $SO_2R^{12}$ in which $R^{12}$ is optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted aryl or optionally substituted heterocycyl and n is 1 to 6;

$R^5$ and $R^7$ are independently selected from H, optionally substituted $C_{1-6}$ alkyl and halo; and r is 1 or 2 or salts, tautomers and/or stereo isomers thereof to a subject in need thereof.

2. The method of claim 1 wherein the effective amount is a specific dosage amount.

3. The method of claim 2 wherein the specific dosage amount is from about 200 to about 800 mg/subject.

4. The method of claim 3 wherein the specific dosage amount is about 500 mg/subject.

5. The method of claim 1 wherein the glioma brain tumour is selected from astrocytoma, glioblastoma multiforme (GBM), anaplastic astrocytoma, mixed glioma and oligodendroglioma.

6. The method of claim 5 wherein the glioma is astrocytoma.

7. The method of claim 5 wherein the glioma is GBM.

8. The method of claim 5 wherein the glioma is anaplastic astrocytoma.

9. The method of claim 1 wherein the compound of formula (IC) is selected from the group consisting of following compounds:

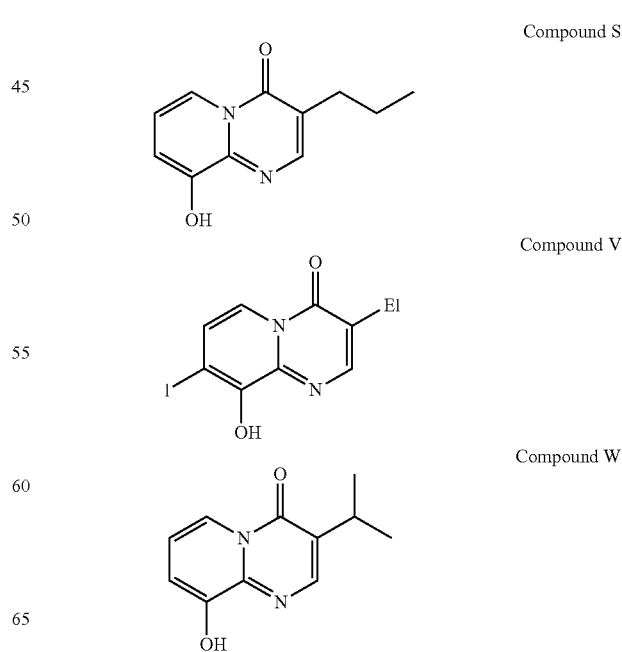

125
-continued
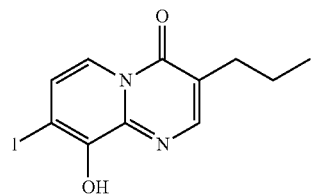
Compound X
and
126
-continued
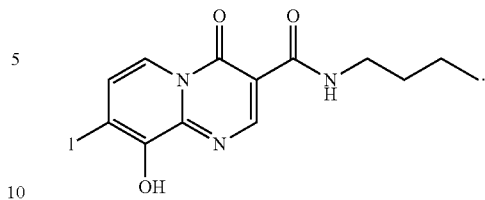
Compound Y
* * * * *